United States Patent
Northington et al.

(10) Patent No.: US 6,464,383 B1
(45) Date of Patent: Oct. 15, 2002

(54) FIBER OPTIC CEILING SUPPORTED SURGICAL TASK LIGHT SYSTEM WITH OPTICAL COMMUTATOR AND MANUAL ZOOM LENS

(75) Inventors: Jay S. Northington; Douglas J. Ansley, both of Montgomery; Samuel E. Davis, Wetumpka; Donald W. Truett, Montgomery, all of AL (US); David Jesurun, South Euclid; Victor M. Selig, Euclid, both of OH (US); Ward L. Sanders, Albion, PA (US); Timothy Kolody, Lorain; Richard L. Hansler, Pepper Pike, both of OH (US); Robert J. Byrd, Marbury; Saysana Say Kongchan, Montgomery, both of AL (US)

(73) Assignee: Steris Inc., Temecula, CA (US)

( * ) Notice: Subject to any disclaimer, the term of this patent is extended or adjusted under 35 U.S.C. 154(b) by 0 days.

(21) Appl. No.: 09/456,660

(22) Filed: Dec. 9, 1999

Related U.S. Application Data

(60) Provisional application No. 60/111,563, filed on Dec. 9, 1998.

(51) Int. Cl.[7] .................................................. A61B 1/06
(52) U.S. Cl. ........................ 362/572; 362/552; 362/804
(58) Field of Search ........................... 362/572, 11, 269, 362/582, 552, 580, 581, 804, 250; 359/227; 342/375; 350/96.24

(56) References Cited

U.S. PATENT DOCUMENTS

| | | | | |
|---|---|---|---|---|
| 3,641,332 A | * | 2/1972 | Reick et al. ................. | 362/582 |
| 3,794,091 A | | 2/1974 | Ersek et al. ................. | 150/52 R |
| 3,809,072 A | | 5/1974 | Ersek et al. ................. | 128/23 |
| 4,037,096 A | * | 7/1977 | Brendgord et al. .......... | 240/1.4 |
| 4,135,231 A | * | 1/1979 | Fisher .......................... | 362/269 |

(List continued on next page.)

FOREIGN PATENT DOCUMENTS

| | | | |
|---|---|---|---|
| DE | 2229683 | * | 2/1974 |
| DE | 21 33 719 B2 | | 12/1977 |
| DE | 21 41 351 B2 | | 1/1979 |
| DE | 28 54 684 B1 | | 2/1980 |

(List continued on next page.)

Primary Examiner—Sandra O'Shea
Assistant Examiner—Bao Truong
(74) Attorney, Agent, or Firm—Fay, Sharpe, Fagan, Minnich & McKee, LLP

(57) ABSTRACT

A surgical task light is provided including a light source adapted to generate light. An elongate optical fiber carries the light generated by the light source to a remote target site. The optical fiber includes a proximal end for receiving the light generated by the light source and a distal end for emitting the light. A support member supports the optical fiber relative to the ceiling of an associated operating room and holds the optical fiber in a plurality of selected positions. A lens device is carried on the distal end of the optical fiber for focusing the light emitted from the distal end of the optical fiber into a desired selected pattern. A sterile sheath member in combination with the surgical task light provides a sterile barrier between the surgical area and the mechanical and optical portions of the task light. A re-lamping module includes a replaceable light bulb module carrying a light bulb to help facilitate replacement of the light bulb by maintenance personnel. A cooling system cools the light bulb and defines an air duct for directing an air flow through heat dissipating members. The air duct is separated from the optical light path between the light bulb and the elongate optical fiber to prevent the air flow from entering the light path to prevent dust and other contaminants from reducing the optical efficiency of the system.

32 Claims, 14 Drawing Sheets

U.S. PATENT DOCUMENTS

| | | | |
|---|---|---|---|
| 4,286,839 A | * 9/1981 | Ilzig et al. | 350/96.24 |
| 4,425,599 A | 1/1984 | Rieder et al. | |
| 4,919,503 A | * 4/1990 | Mroynski | 350/96.2 |
| 5,078,466 A | 1/1992 | MacCulloch | |
| 5,230,555 A | 7/1993 | Stephenson et al. | |
| 5,295,052 A | 3/1994 | Chin et al. | |
| 5,299,053 A | * 3/1994 | Kleinburg et al. | 359/227 |
| 5,337,734 A | 8/1994 | Saab | 128/4 |
| 5,347,288 A | * 9/1994 | Page | 342/375 |
| 5,347,431 A | * 9/1994 | Blackwell et al. | 362/11 |
| 5,443,781 A | 8/1995 | Saab | 264/291 |
| 5,450,509 A | 9/1995 | Davis | |
| 5,497,295 A | * 3/1996 | Gehly | 362/572 |
| 5,621,830 A | 4/1997 | Lucey et al. | |
| 5,653,897 A | 8/1997 | Findlan et al. | |
| 5,709,459 A | * 1/1998 | Gourgouliatos et al. | 362/105 |
| 5,792,045 A | 8/1998 | Adair | |
| 5,871,268 A | 2/1999 | Edens et al. | |
| 5,887,965 A | 3/1999 | Edens et al. | |
| 5,970,980 A | 10/1999 | Adair | |
| 5,971,916 A | 10/1999 | Koren | |
| 5,997,047 A | 12/1999 | Pimentel et al. | |
| 5,997,165 A | 12/1999 | Lehrer | |
| 6,000,400 A | 12/1999 | Navis | |

FOREIGN PATENT DOCUMENTS

| | | |
|---|---|---|
| DE | 29 30 308 A1 | 1/1981 |
| DE | 40 33 625 A1 | 4/1992 |
| DE | 93 06 771.2 | 8/1993 |
| EP | 0 066 901 A2 | 12/1982 |
| EP | 0 304 564 A1 | 3/1989 |

* cited by examiner

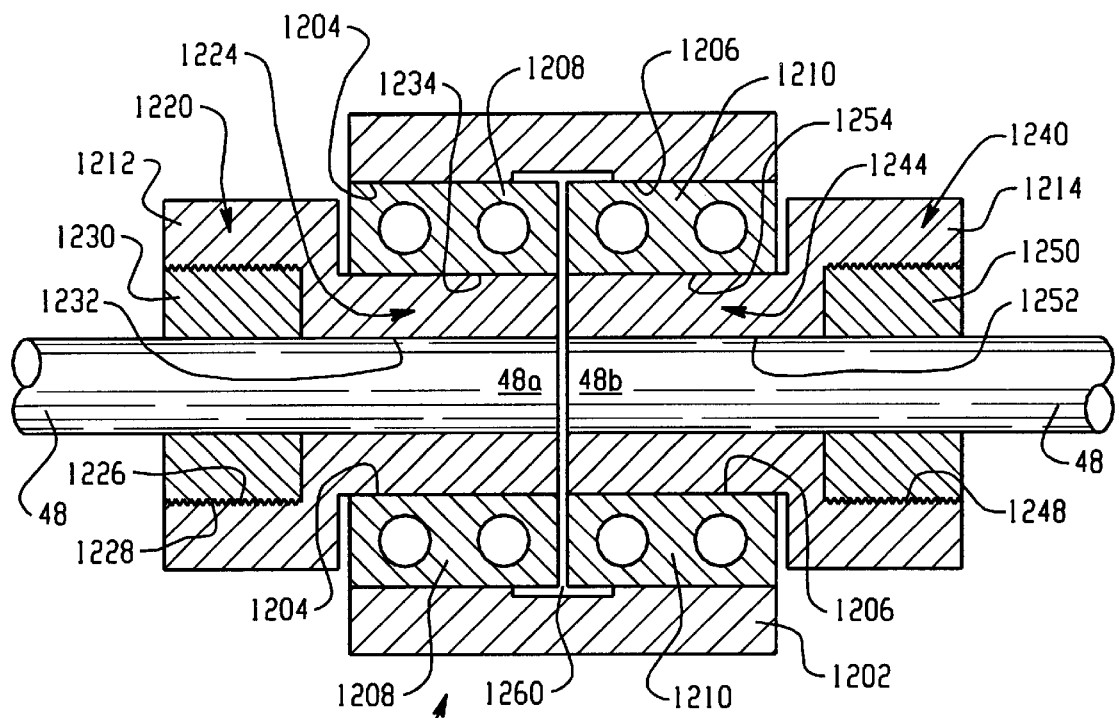
Fig. 14
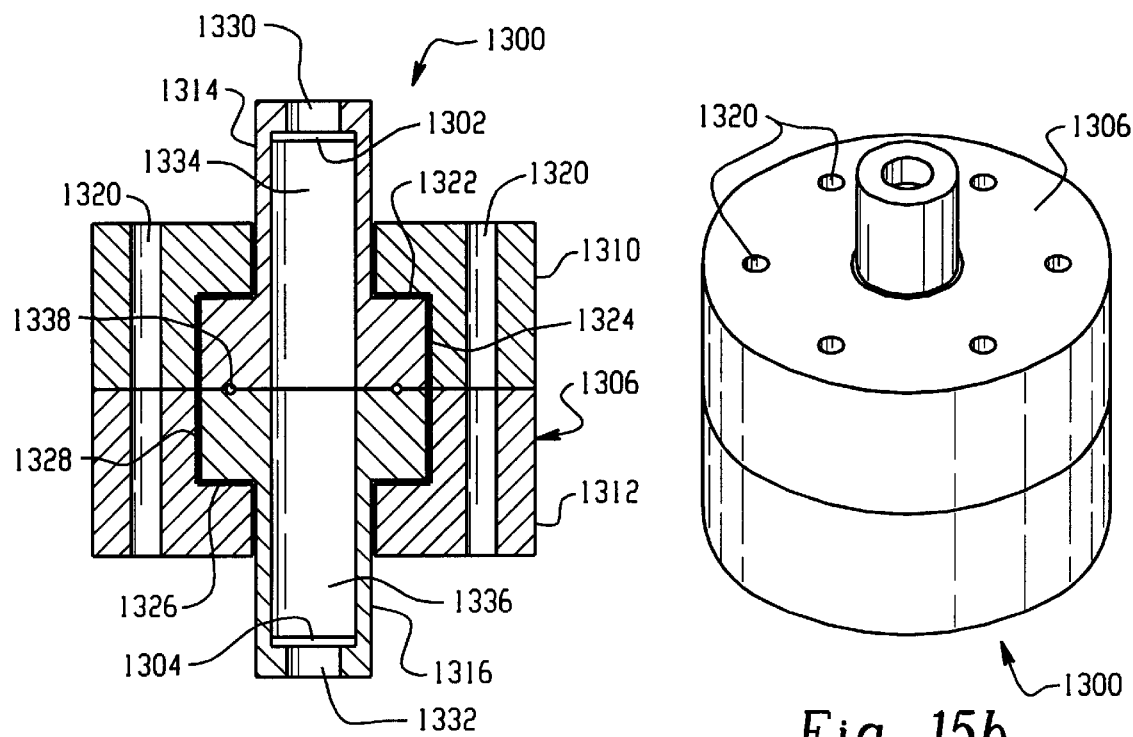
Fig. 15a
Fig. 15b

US 6,464,383 B1

FIBER OPTIC CEILING SUPPORTED SURGICAL TASK LIGHT SYSTEM WITH OPTICAL COMMUTATOR AND MANUAL ZOOM LENS

CROSS-REFERENCE TO RELATED APPLICATION

This application claims the benefit of U.S. Provisional Application Serial No. 60/111,563 filed Dec. 9, 1998.

BACKGROUND OF THE INVENTION

The present invention is directed to the art of lighting systems, and, more particularly, to lighting apparatus of the type adapted for particular use in surgical procedures. The invention will be described in connection with the preferred surgical task light suspended from overhead at the ceiling of an operating room but it is to be appreciated that the invention has broader application and can be applied in numerous settings and suspended using a wide range of mechanical components such as wall and floor mounts, and the like.

Typical surgical rooms include one or more fairly large lighthead devices suspended from the ceiling on one or more articulated arm members. Because of the amount of light demanded from the lightheads, they have, over the years, become fairly large and bulky. Low shadow considerations as well as automatic on-the-fly expired bulb replacements have further added to the size and weight of typical surgical lightheads.

Although typical surgical lightheads have proved adequate in most situations, certain surgical procedures require spot-sized light to be shined at awkward angles such as, for example, into certain body cavities of the patient while disposed on a surgical table. As noted above, standard surgical lightheads are fairly large in size and, accordingly, are sometimes difficult to maneuver into an appropriate position adjacent the patient to develop suitable light spots in the desired body cavities or the like.

In addition to the above, typical surgical lightheads are provided with only a single light power setting. More particularly, a single light source disposed within the surgical lighthead is selectively connected to a external power source using a simple switch mechanism. This being the case, the light source is either connected to the power source for generating light or disconnected therefrom and placed in an inactive state. Variable power ranges that are selectable between a full "ON" position and a full "OFF" position have not been commercially available.

Therefore, it is desirable to provide a surgical lighting device that enables the development of light rays that can be directed into patient body cavities, or the like, from extreme or awkward positions in the surgical room.

In addition, it is desirable to provide a task light that is manually manipulated into a plurality of desired positions adjacent a patient's body for developing a light spot to augment the light provided by the standard overhead lightheads.

Still further, it is desirable to provide a surgical task light that generates a selectable range of intensity levels so that the surgeon can regulate the amount of light falling onto a desired target point within the patient.

SUMMARY OF THE INVENTION

In accordance with the present invention, a surgical task light is provided including a light source adapted to generate light. An elongate optical fiber is adapted to carry the light generated by the light source to a selectable destination, preferably towards a surgical site. The elongate optical fiber includes a proximal end for receiving the light generated by the light source and a distal end for emitting the light. A support member is adapted to support the optical fiber relative to a ceiling of an associated operating room. The support member is further adapted to hold the optical fiber in a plurality of selected positions relative to the surgical site. A lens device is carried on the distal end of the optical fiber for focusing the light emitted from the distal end of the optical fiber into a desired selected pattern.

In accordance with an aspect of the invention, the subject surgical task light system further includes an optical commutator for dividing the elongate optical fiber into a first portion and a second portion. The optical commutator enables relative rotational movement between the first and second portions of the elongate optical fiber to provide for flexibility in the support member.

Still further in accordance with the invention, a shutter device is provided in operative association with the light source. The shutter device controls an amount of the light delivered from the light source to the lens device. Preferably, the shutter device includes a rotatable cylindrical member defining a tapered passageway opening for delivering the light from the light source to the lens device in an amount based on a rotational position of the cylindrical member. Preferably, the relationship between the rotational position of the cylindrical member and the amount of light delivered from the light source to the lens device is linear.

In accordance with a further aspect of the invention, the support member of the subject surgical task lighting includes an elongate gooseneck portion carrying the lens device and formed of a plurality of interlocking joint members, the gooseneck portion being manually manipulatable into a plurality of selected orientations and being adapted to hold position in said plurality of selected orientations to hold the lens device stationary at a desired selected position.

In accordance with a more limited aspect of the invention, the light source includes a re-lamping module for ease of replacement of a light generating means by maintenance personnel. The re-lamping module includes a replaceable light bulb module and a set of heat sink members carrying the replaceable light bulb module. The set of heat sink members are adapted to conduct heat from the replaceable light bulb module and, in addition, are adapted to conduct electrical power from an operatively associated source of power to the replaceable light bulb module.

In accordance with yet a further more limited aspect of the invention, the replaceable light bulb module includes an electrically conductive main body member adapted for selective connection to at least one of the heat sink members. Further, the replaceable light bulb module includes a light bulb carried on the electrically conductive main body member. Lastly, a manual grip portion is formed on one end of the electrically conductive main body member. The manual grip portion is preferably thermally insulative so that the replaceable light bulb module can be removed from the re-lamping module while the light bulb is still hot. The manual grip portion provides a manually grippable surface for selective manual removal of the replaceable light bulb module from the light source.

Still further in accordance with the invention, a sterile sheath member is provided in combination with the subject surgical task light. The sterile sheath member includes a light opaque portion adapted to transmit light therethrough and an elongate substantially tubular cover member connected on one end to the light opaque portion. The sterile sheath member is adapted for connection onto the surgical task light to enable the task light to be used in sterile procedures. First, the light opaque portion is connected onto the lens device to enable light to pass from the lens device and through the light opaque portion onto the surgical site. Next, the tubular cover member is selectively extended over the support member and tied or otherwise fastened thereto to provide a protective barrier between the surgical task light and the sterile field while simultaneously not obstructing the light emitted from the distal end of the optical fiber and focused by the lens device.

It is a primary object of the invention to provide a surgical task light of the type described including an elongate optical fiber to court light from a remote site onto a sterile surgical field.

It is another object of the invention to provide a surgical task light of the type described including a support member adapted to support the optical fiber relative to the surgical site so that light emitted from the distal end of the optical fiber can be directed into the surgical site at a variety of positions and orientations.

It is still yet another object of the invention to provide a lens device carried on the distal end of the optical fiber for focusing the light emitted from the distal end of the optical fiber into a desired selected pattern.

Still further, it another object of the invention to provide, in combination with the surgical task light, a sterile sheath member for providing a barrier between the surgical task light and the sterile surgical field. Preferably, the sterile sheath member includes a light opaque portion and an elongate substantially tubular cover member that is extendable onto the support member and fastened thereto using ties or other means.

Still yet another object of the invention is to provide a re-lamping module including a replaceable light bulb module to help facilitate light bulb replacement in the subject surgical task light.

These and other objects, advantages, and benefits of the invention will become apparent to those skilled in the art upon a reading and understanding of the following detailed description.

BRIEF DESCRIPTION OF THE DRAWINGS

The invention may take physical form in certain and arrangements of parts, a preferred embodiment of which will be described in detail in this specification and illustrated in the accompanying drawings which form a part hereof, and wherein:

FIG. 14 is a cross-sectional view of an alternative optical commutator device for use in the subject surgical task light system shown in FIG. 1;

FIGS. 15a and 15b show a perspective view and a cross-sectional view, respectively, of another alternative optical commutator device for use in the subject surgical task light system shown in FIG. 1;

DETAILED DESCRIPTION OF THE PREFERRED EMBODIMENT

Figure 1:
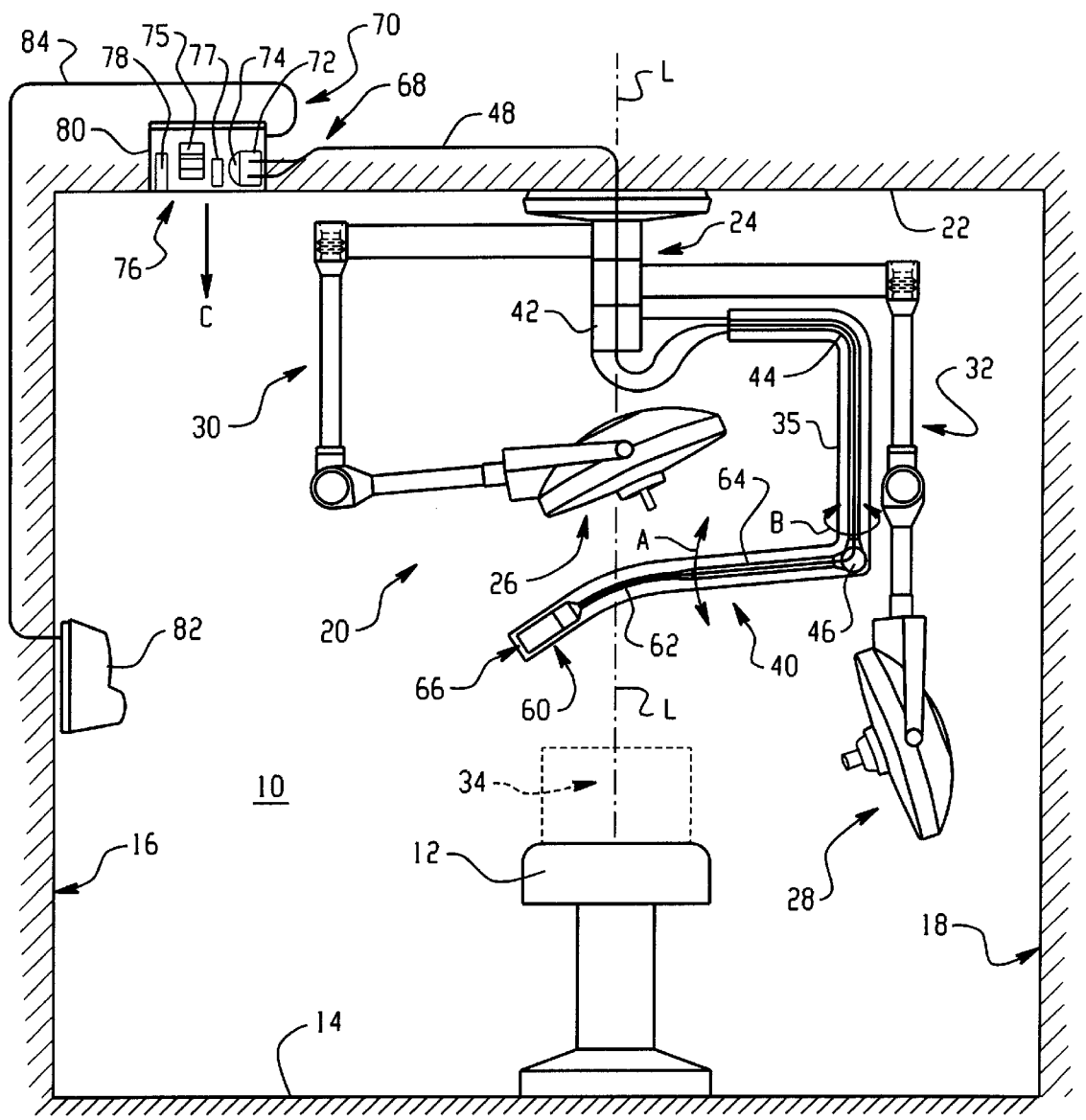
FIG. 1 is a schematic view of a surgical room including the fiber optic surgical task light system formed in accordance with the present invention.

Referring now to the drawings wherein the showings are for the purposes of illustrating the preferred embodiment of the invention only and not for purposes of limiting same, FIG. 1 shows an operating room 10 equipped with a surgical table 12 free standing on the floor 14 between left and right walls 16, 18. The table is centered under a surgical lighting system 20 that is supported from the ceiling 22 of the operating room from a central rotary hub device 24. A pair of surgical lightheads 26, 28 are each respectively attached to the rotary hub device 24 through a corresponding set of support arm members 30, 32 using techniques and components that are well known and available in the art. The lightheads illuminate a surgical site 34 adjacent the surgical table.

In accordance with the instant application, a fiber optic ceiling supported task light system 40 is provided as an auxiliary lighting system to augment the illumination developed by the first and second surgical lightheads 26, 28. The task light may also be used by itself or with a single surgical lighthead. Preferably, the task light generates a cold beam of light having a spot size between 2 and 6 inches.

With continued reference to FIG. 1, the fiber optic surgical task light is supported from the ceiling 22 by a lower mechanical rotary hub member 42 that is connected as shown to the central rotary hub device 24 described above. In the embodiment illustrated, the rotary hub member 42 may be rotated continuously about the longitudinal axis L defined by the rotary hub device 24. The hub member 42 freely moves through multiple rotations without any mechanical binding or interference by means of an optical commutator device and suitable mechanical bearings and the like so that the task light supported therefrom can be moved into any desirable orientation. Alternatively, the optical commutator can be eliminated to improve the optical efficiency of the system. In that case, the extent of rotary motion of the rotary hub member 42 would, of course, be limited to less than 360°, for example 340°.

An elongate L-shaped support member 44 is connected on one end to the mechanical rotary hub member 42 and, on the other end, to a mechanical compound counterbalanced joint member 46. The L-shaped member 44 is substantially hollow to enable an elongate fiber optic cable 48 to be carried therein. In that way, the fiber optic cable is concealed within the L-shaped support member. The fiber optic cable 48 extends from the bottom of the rotary hub member 42 and then is routed directly into the L-shaped support member. In that way, none of the fiber optic cable is exposed. The cable can be reached, however, by use of an access panel (not shown) or the like provided on the hub member 42.

The lower portion of the fiber optic task light system 40 includes a manual zoom lens device 60 carried on a flexible goose neck 62 which is in turn supported from the mechanical compound counterbalanced joint member 46 by a rigid elongate support member 64. The support member 64 and flexible goose neck 62 carry the lower portion of the fiber optic cable 48 so that the mechanical zoom lens device 60 can be used to emit light from a distal end 66 thereof onto the surgical site 34.

In order to allow the zoom lens device to be positioned and adjusted by sterile members of the surgical team, a disposable sterile cover 35 is provided over the zoom lens device. In the preferred embodiment, a transparent plastic cap is carried in a plastic fitting cap that is shaped to conform to the distal end of the zoom lens device. A loose fitting polymer portion having good fictional properties extends from the fitting cap and along the lens device 60. A tubular plastic portion is connected on one end to the fitting cap. The sheath is attached prior to use by force fitting the resilient plastic cap member onto the zoom lens device. One end of the flexible sterile sheath is attached to the plastic cap. The free end of the sheath is adapted to be unfurled and pulled up over the device covering the gooseneck and suspension system to prevent contamination of the sterile surgical team members in the event of contact with the device.

It is to be noted that the joint member 46 provides compound motion between the L-shaped member 44 and the elongate support member 64 allowing the elongate support member 64 to both raise/lower and pivot. In that regard, a shoulder joint portion of the joint member enables pivotal movement of the elongate support member 64 in the direction labeled A in FIG. 1. A wrist portion of the mechanical compound joint member enables rotary motion of the elongate support member 64 in the direction labeled B in FIG. 1. A counterbalance mechanism known in the art (not shown) is disposed within the joint member 46 to support some of the weight of the elongate support member 64, flexible gooseneck 62 and mechanical zoom lens device 60, thus reducing the force required to raise the mechanism. An adjustable friction braking mechanism known in the art (not shown) is also disposed within the joint member 46 to keep the joint from drifting under the force of gravity when the positioning force is no longer being applied.

In the preferred embodiment illustrated, the rotary motion B of the lower portion of the fiber optic task light below the mechanical compound joint member 46 is unrestricted. To prevent damage to the fiber optic cable that would result from rotary motion B, an optical commutator (not shown) is disposed at the rotary joint portion of the mechanical compound joint member 46 or in member 44. The optical commutator enables multiple full 360° degree rotations of the elongate support member 64 and of manual zoom lens device 60 carried thereon during surgical procedures and the like without twisting or winding the fiber optic cable 48. One or more energy chain devices (not shown) are included in members 44 and 46 as needed to assist in preventing the fiber optic cable 48 from kinking within the task light system support members.

The proximal end 68 of the fiber optic cable 48 is received in an illuminator box device 70 adapted for placement within the ceiling 22 of the operating room 10 as shown. An attachment joint 72, a lens 74, a light source 75 integrated in a re-lamping module 76, a mechanical shutter device 77, and a cooling system 78 are disposed in a rigid enclosure box 80 of the illuminator device 70 as shown. Preferably, the components within the enclosure box 80 are RF shielded. The components of the re-lamping module 76 are arranged in the enclosure box 80 to provide convenient access to the light source whenever there is a need to replace the bulb or to perform other servicing or periodic maintenance. The re-lamping module is selectively slidable outwardly from the enclosure box 80 in the direction labeled C in the drawing towards a stop position. The suspended module allows easy access to the lamp.

Lastly in connection with FIG. 1, a variable intensity controller 82 is arranged on the wall 16 of the operating room 10 within reach of the surgeon or other operating room personnel as shown. The variable intensity controller is operatively connected to the mechanical shutter device 77 in the illuminator box device 70 by a control cable 84 that extends through the wall and ceiling 16, 22 of the operating room as shown. The variable intensity controller includes a control panel with a manual push button membrane keypad that is connected to the illuminator box device 70 to enable convenient light intensity control to be effected remotely by surgeons or other operating room personnel. The illuminator box contains a direct current D.C. positioning motor and drive (not shown) which spin a metal cylinder having a specially formed opening through a range of selected angles. The shutter device 77 is disposed in the path of the light beam to accomplish light intensity control.

Figure 2:
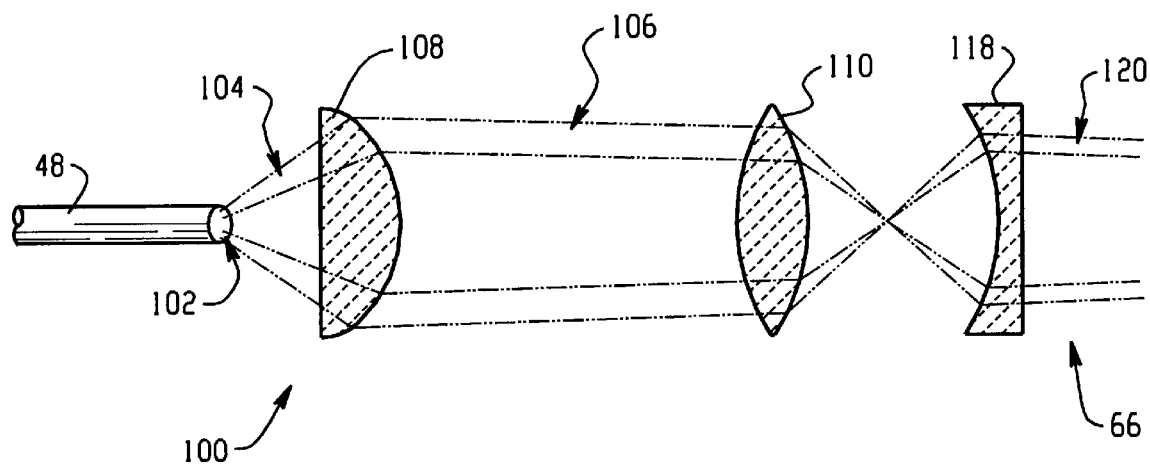
FIG. 2 is a simplified schematic view of an optical system used in a portion of the fiber optic surgical task light system shown in FIG. 1.

FIG. 2 is a basic diagrammatical illustration of the optical system 100 used within the manual zoom lens device 60 described above. With reference now to that figure, light is emitted from the distal end 102 of the optical fiber 48 creating a divergent light ray 104 as shown. The divergence of the light ray 104 is reduced by means of a short focal length aspheric condensing lens 108 which in the preferred embodiment has a focal length of about 10 mm–20 mm. The distance from the end of the optical fiber end 102 is less than the back focal length of lens 108, so full collimation is not obtained, but a virtual image of the end of the optical fiber is produced. By adjusting this distance, the ultimate spot size and range of spot size produced by the zoom lens is controlled. By reducing the divergence of the light rays with lens 108, a large fraction of the light coming from the end of the optical fiber strikes the movable focusing lens 110. Preferably, the focusing lens 110 is a positive lens having a symmetric convex form with a focal length within the range of about 50 mm–100 mm. The stationary output lens 118 is a negative lens which in the preferred embodiment is a meniscus lens of about 125 mm–200 mm focal length. These two lenses 110 and 118 operate together to form an image of the end of the optical fiber as magnified by lens 108. When the positive lens 110 is close to the output lens 118 the lens set has the highest power (shortest effective focal length) and forms a small image of the end of the optical fiber. When lens 110 is moved to a position about half way between lens 108 and lens 118 the power of the combination is reduced (longer effective focal length) and the image of the end of the fiber is larger. At a distance of about 15 to 22 inches, the spot size may be varied from about 2 to 6 inches in diameter as lens 110 is moved.

In a second embodiment described below in detail, both the lens 110 and 118 are moved relative to lens 100 and to each other. This allows the sharpness of focus of the image of the end of the optical fiber to be more fully preserved over the range of spot size than when only the 110 lens is moved.

In the optical system 100 shown in FIG. 2, the light emitted from the distal end of the output lens is generally divergent and preferably creates a 2–6 inch spot size on a surface disposed between 15 and 22 inches from the end of the zoom lens device. The divergent nature of the emitted light beam 120 is controllable by adjusting the relative position between the focusing lens 110 and the output lens 118. As can be seen from the illustration, the emitted light beam 120 broadens, or diverges, as the relative distance between the focusing lens and the output lens is increased. This has the effect of increasing the spot size on the surgical site 34. When the relative spacing between the focusing lens 110 and the output lens 118 is decreased, the emitted light beam 120 tends to narrow, or converge. This has the effect of reducing the spot size in the surgical site 34.

Figure 3:
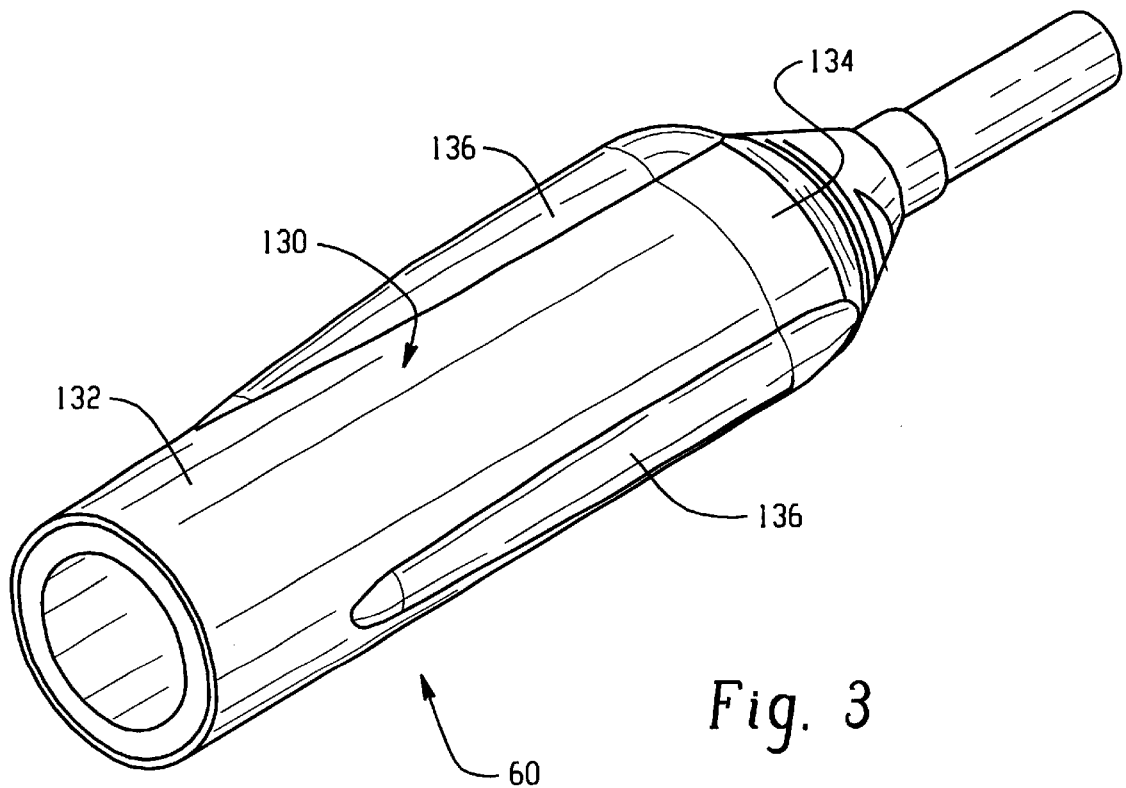
FIG. 3 is a perspective view of a manual zoom lens device used on the distal end of the surgical task light system shown in FIG. 1.
Figure 4:
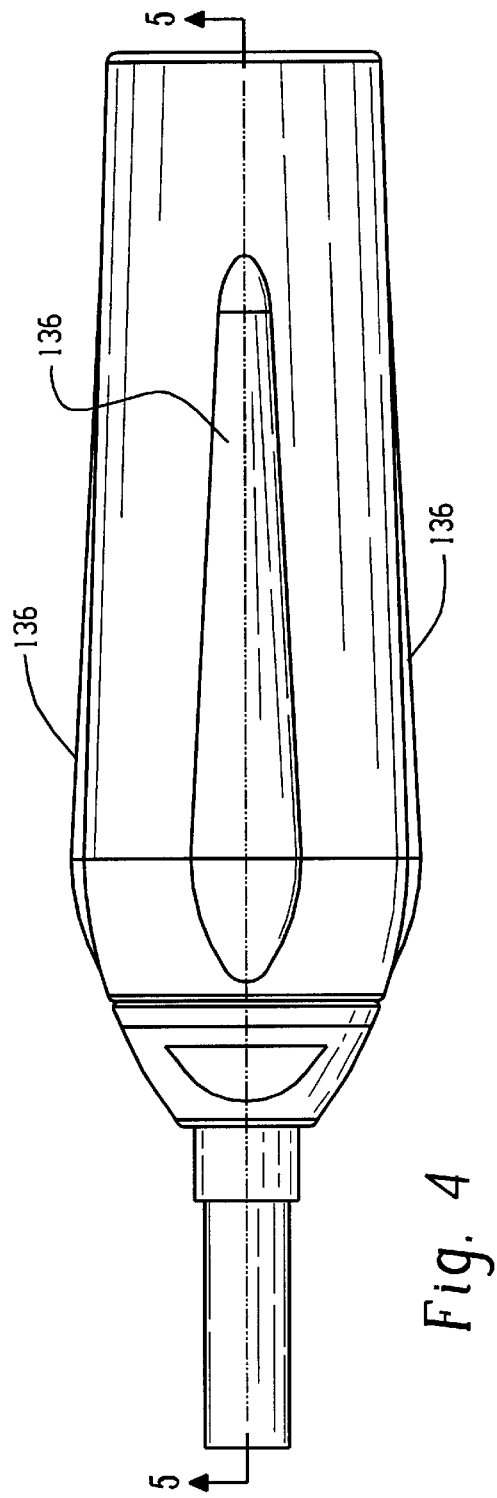
FIG. 4 is an elevational side view of the manual zoom lens shown in FIG. 3.

FIGS. 3–6 illustrate the manual zoom lens device 60 of the subject surgical task light system in various stages of assembly and disassembly and in exploded and cross sectional views. Referring first to FIGS. 3 and 4, the manual zoom lens device 60 includes a two-piece outer housing 130 that includes an elongate substantially cylindrical grip member 132 and an end piece portion 134. The outer housing 130 preferably includes a plurality of longitudinally extending and outwardly formed grip ribs 136 to help facilitate manual manipulation of the zoom lens device 60. In the preferred embodiment illustrated, the ribs extend substantially along the entire length of the two-piece outer housing 130 and therefore traverse both the grip member portion 132 and the end piece 134 portion.

Figure 5:
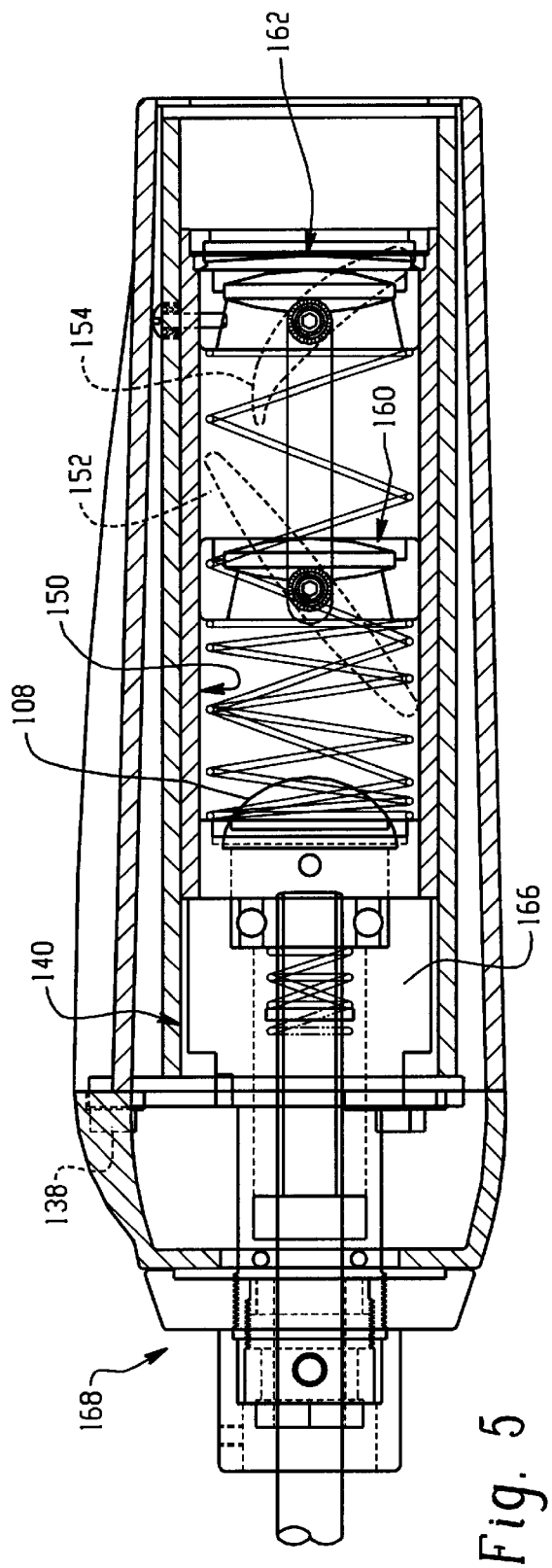
FIG. 5 is cross-sectional view of the manual zoom lens device shown in FIG. 4 taken along line 5—5.

As shown best in FIG. 5, the plurality of ribs 136 provide a convenient location to enable engagement between the grip member and the end piece portion without any resulting exposed fastening members. In that regard, a set of capscrews 138 are used to engage the grip member and end piece together for rotational movement and further to connect the grip to a circular drive member 140. The circular drive member 140 is in turn connected to an elongate substantially cylindrical outer drive tube 142 using a set of suitable fasteners 144. Preferably, the grip member 132 and the end piece 134 are secured together axially by a back nut 168 to be described in more complete detail below.

Figure 6:
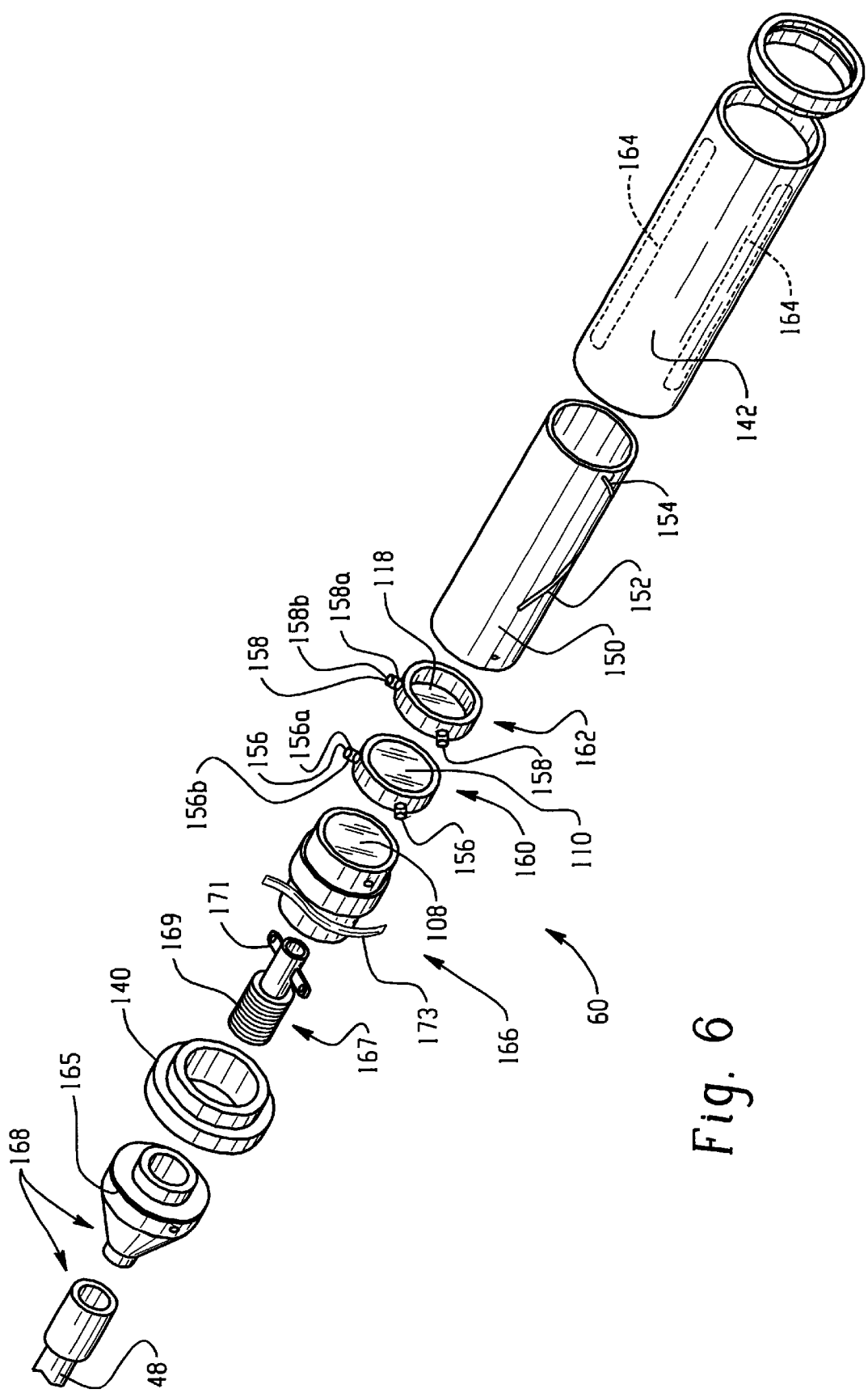
FIG. 6 is an exploded view of the manual zoom lens device shown in FIG. 3 with the outer covering removed to illustrate the internal working components thereof.

As shown best in FIGS. 5 and 6, a cylindrical outer drive tube 142 closely encircles an inner cylindrical slotted tube 150. In the preferred embodiment illustrated, the inner slotted tube includes a pair of oppositely directed helical slots 152, 154 that are adapted to receive a set of radially extending drive pin members 156, 158 formed on first and second lens carrier assemblies 160, 162, respectively. The radially extending drive pin members 156, 158 are provided having sufficient length so that they extend completely through the helical slots 152, 154 of the inner cylindrical slotted tube 150 and beyond into a set of longitudinally extending slots 164 defined on the inner surface of the cylindrical outer drive tube 142. Preferably, as shown, each of the first and second set of radially extending pin members 156, 158 carry a pair of stacked bearing members 156a, 156b and 158a, 158b as shown. The radially outward bearings 156b and 158a are disposed for smooth engagement with the slots 164 formed in the outer drive tube 142. The radially inner bearings 156a and 158b are disposed for smooth engagement with the helical slots 152 and 154 formed in the inner slotted tube 150. In an alternative embodiment where only a single lens 110 is removed, only a single helical slot 152 is provided.

The first lens carrier 160 carries the focusing lens 110 and the second lens carrier assembly 162 carries the output lens 118. The input lens 108 is held in place by a cylindrical interface member 166 as best shown in FIG. 5.

In use of the subject manual zoom lens device, the inner cylindrical slotted tube 150 remains generally fixed in place relative to the cylindrical interface member 166 and rotatably coupled to the zoom lens device through a cable grasp member 168. Accordingly, manual rotation of the two-piece outer housing 130 urges the cylindrical outer drive tube 142 into rotation relative to the inner cylindrical slotted tube 150. The relative movement between the helical slots 152, 154 formed in the inner cylindrical slotted tube 150 and the longitudinally extending set of slots 164 formed in the cylindrical outer drive tube 142 in turn urge the drive pin members 156, 158 into motion. The first and second lens carrier assemblies 160, 162 are thereby correspondingly helically moved relative to each other. Since the helical slots are oppositely formed for two lens movement, the focusing and output lenses are moved toward and away from each other as the zoom lens device 60 is manipulated by twisting the two-piece outer housing. For single lens motion, the single helical slot 152 moves the focusing lens relative to the stationary output lens.

A Teflon slip washer 165 provides a low friction surface interface between the cable grasp member 168 and the drive member 140. A ferrule member 167 includes, on one end, threads 169 to enable axial adjustment of the distance between the optical fiber end and the lens 108. A second end of the ferrule member 167 is rotatable relative to the member 166 and includes optical fiber clamp means 171 for connection to the fiber optic cable 48. A spring member 173 biases the distal end of the fiber optic cable 48 towards the lens bearing located at the end of member 167.

Figure 7:
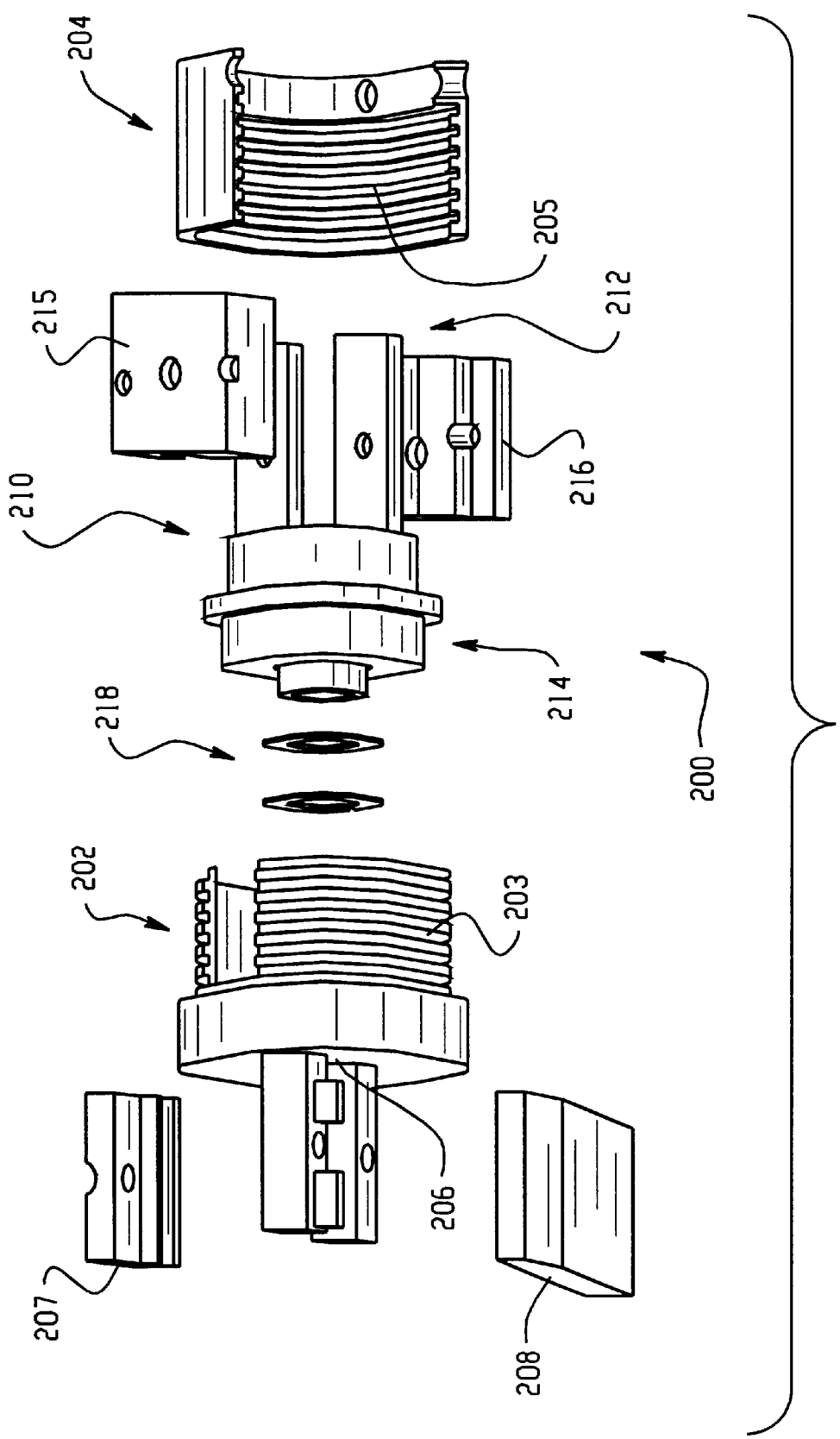
FIG. 7 is an exploded view of a preferred optical commutator device used in the fiber optic surgical task light system shown in FIG. 1.

Turning now to FIG. 7, the optical commutator device 200 used in the preferred embodiment of the invention will be described. Generally, the commutator device 200 includes first and second main body members 202, 204 that include threaded portions 203 and 205, respectively for selective connection of the body member. As shown, the first main body member 202 includes an externally threaded portion 203 and the second main body member 204 includes the corresponding internally threaded portion 205.

It is to be appreciated that the first main body member 202 includes a central axial passageway 206 extending therethrough. The passageway 206 is adapted to receive a first end of the fiber optic cable 48 therethrough. The cable is held in place relative to the first main body member 202 by means of a pair of opposing clamp members 207, 208 that are selectively connected to the first main body member using any suitable fasteners or the like.

With continued reference to FIG. 7, the subject commutator 200 includes a third main body member 210 having, on one end, a clamping portion 212 and, on the other end, a bearing member 214. It is to be appreciated that the clamping portion 212 of the third main body member 210 is formed substantially similar to the first main body member 202 so that a second free end of the fiber optic cable can be securely fastened to the third main body member. To that end, a pair of opposing clamp members 215, 216 are selectively clamped together at the clamping portion using suitable fasteners or the like to hold the second free end of the fiber optic cable in place relative to the third main body member 210. A pair of clips 218 are preferably used to hold the bearing member 214 in place on the third main body member 210.

It is further to be appreciated that a first free end of the fiber optic cable is first fastened to the first main body member 202 using the first and second opposing clamp members 207, 208. Next, the second free end of the fiber optic cable is connected to the third main body member 210 using the pair of opposing clamp members 215 and 216. Thereafter, the third main body member 210 carrying the fiber optic cable and the bearing member 214 is inserted into the first main body member 202 so that the bearing member 214 engages an internal surface (not shown) formed by the first main body member 202. Preferably, the bearing member enables relative rotational movement between the first and third main body members 202, 210. In order to hold the third main body member in place relative to the first main body member, the second main body member 204 is threadedly connected onto the first main body member using the respective threaded portions 203, 205 thereof. Preferably, the free ends of the fiber optic cable are held in precise longitudinal and axial alignment by the commutator device 200 while simultaneously enabling relative rotation as needed to move the subject task light system 40 into selected positions relative to the surgical site 34. As noted above, one or more commutators 200 are used in the subject task light system 40 to provide a wide range of movement and flexibility.

Figure 8:
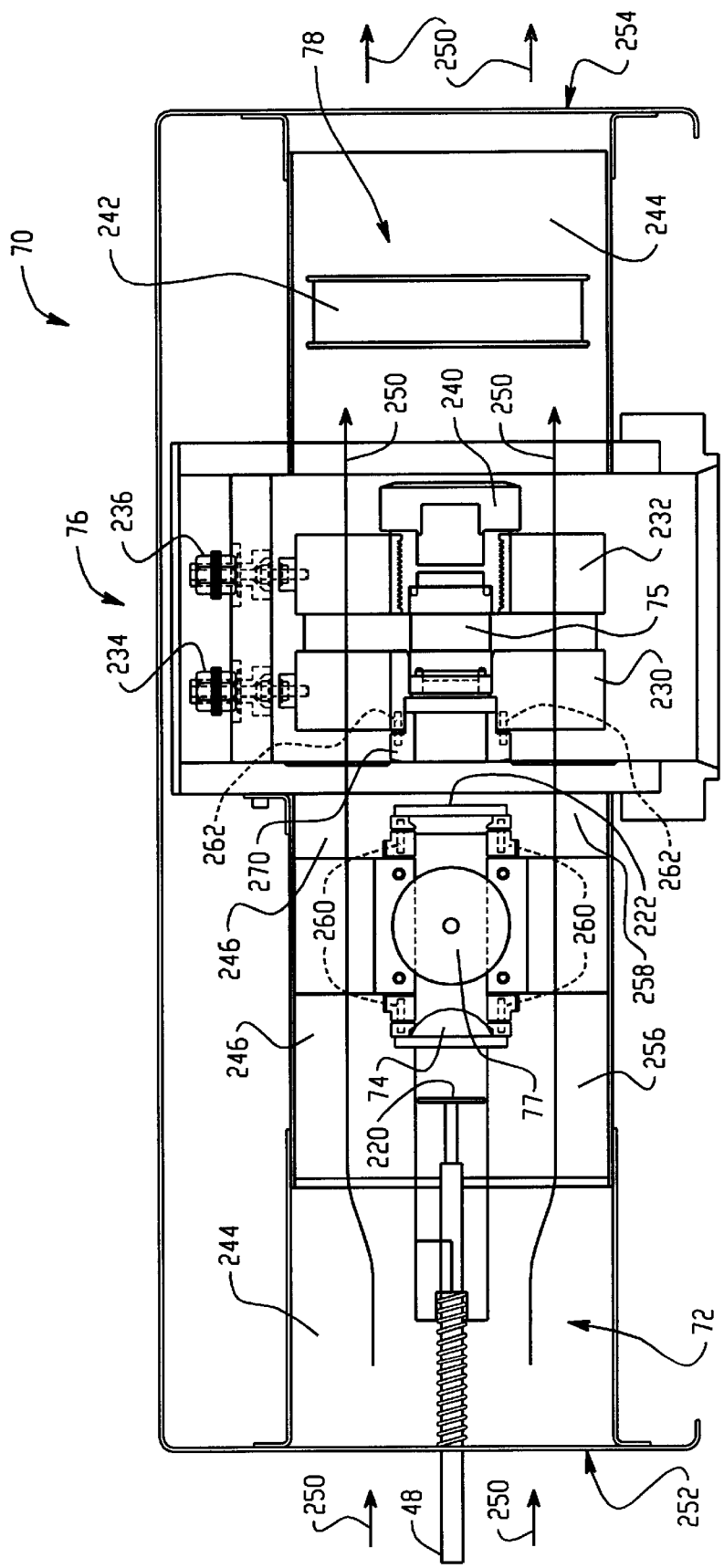
FIG. 8 is a cross-sectional view of a preferred sealed optical portion of an illuminator box device used in the system shown in FIG. 1.

FIG. 8 shows the third form of the sealed optical system 70 for use in the subject surgical task light system in accordance with the present invention. With reference now to that figure, the illuminator box device 70 includes an attachment joint portion 72 for attaching a free end of the fiber optic cable 48 to the illuminator box device 70. A focusing lens 74 receives light generated by a light source 75 and focuses the light generated thereby onto the free end 220 of the fiber optic cable 48. A mechanical shutter device 77 is disposed between the light source 75 and the focusing lens 74 for providing control over the intensity of light delivered to the manual zoom lens device 60 downstream. In addition, a "hot" mirror device 222 is disposed between the light source 75 and the focusing lens 74 for reflecting infrared energy generated by the lamp 75 in order to protect the fiber optic cable 48, as well as the surgical site 34, from excess heat. Preferably, the hot mirror includes an infrared reflective material disposed on a substrate formed of an infrared absorbing filter material. In that way, while some of the I.R. energy is absorbed into the improved absorbing filter, infrared energy is reflected back toward the lamp 75 while cool light is delivered onto the free end 220 of the fiber optic cable 48.

With yet continued reference to FIG. 8, the illuminator box device 70 includes a re-lamping module 76 including first and second heat sink members 230, 232 disposed on opposite sides of the light generating member 75. In accordance with the present invention, the re-lamping module 76 is selectively manually slidable relative to the illuminator box device 70 to enable easy replacement of the light source 75. In addition, it is an advantage of the present invention that the first and second heat sink members 230, 232 provide both thermal conduction of energy away from the light source 75 as well as conduction of electric energy into the light source 75. More particularly, preferably, the first and second heat sink members 230, 232 are formed of aluminum and are selectively connectable to first and second power connectors 234, 236, respectively. Thus, removal of the re-lamping module 76 from the illuminator box device 70 provides a disconnection of the light source 75 from an associated power source. Further simplification of light source replacement is enabled by a replaceable lamp module portion 240 shown in the figure in selective threaded engagement with the second heat sink member 232. The details of the re-lamping module 76 will be discussed in greater detail below.

With yet continued reference to FIG. 8, the illuminator box device 70 includes a cooling system 78 including an electric cooling fan 242, a central transverse air duct 244, and a plurality of cooling fins 246 formed integrally with the various components comprising the illuminator box device 70. Overall, the cooling system 78 establishes an air flow 250 that enters the illuminator box device at an opening 252 and exits the device at an exhaust opening 254.

It is to be appreciated that in accordance with the present invention, the air flow 250 is substantially entirely sealed off from the optical components forming the subject surgical task light system. More particularly, to that end, the mechanical shutter device 77 is held between first and second block members 256, 258 using suitable sealing spring members 260 as shown. In that way, the air flow 250 passes through the cooling fins 246 formed by the block members 256, 258 and around the mechanical shutter device 77 without ingress into the optical path formed between the light source 75 and the free end 220 of the fiber optic cable 48. Separation between the cooling air flow and the optical path is extremely advantageous in improving the overall optical efficiency of the system by discouraging the formation of dust and other contaminants that might otherwise adversely affect the optical characteristics of the light transmission path.

Further to the above, a second set of spring members 262 are provided at the re-lamping module 76 as shown to preload an annular engagement member 270 against the face surface 272 of a housing 274 adapted for selectively receiving the re-lamping module 76. In that way, the selective removal and replacement of the re-lamping module 76 into the housing 274 of the illuminator box 70 is possible without compromising the separation between the air flow 250 and the optical path.

Figure 9:
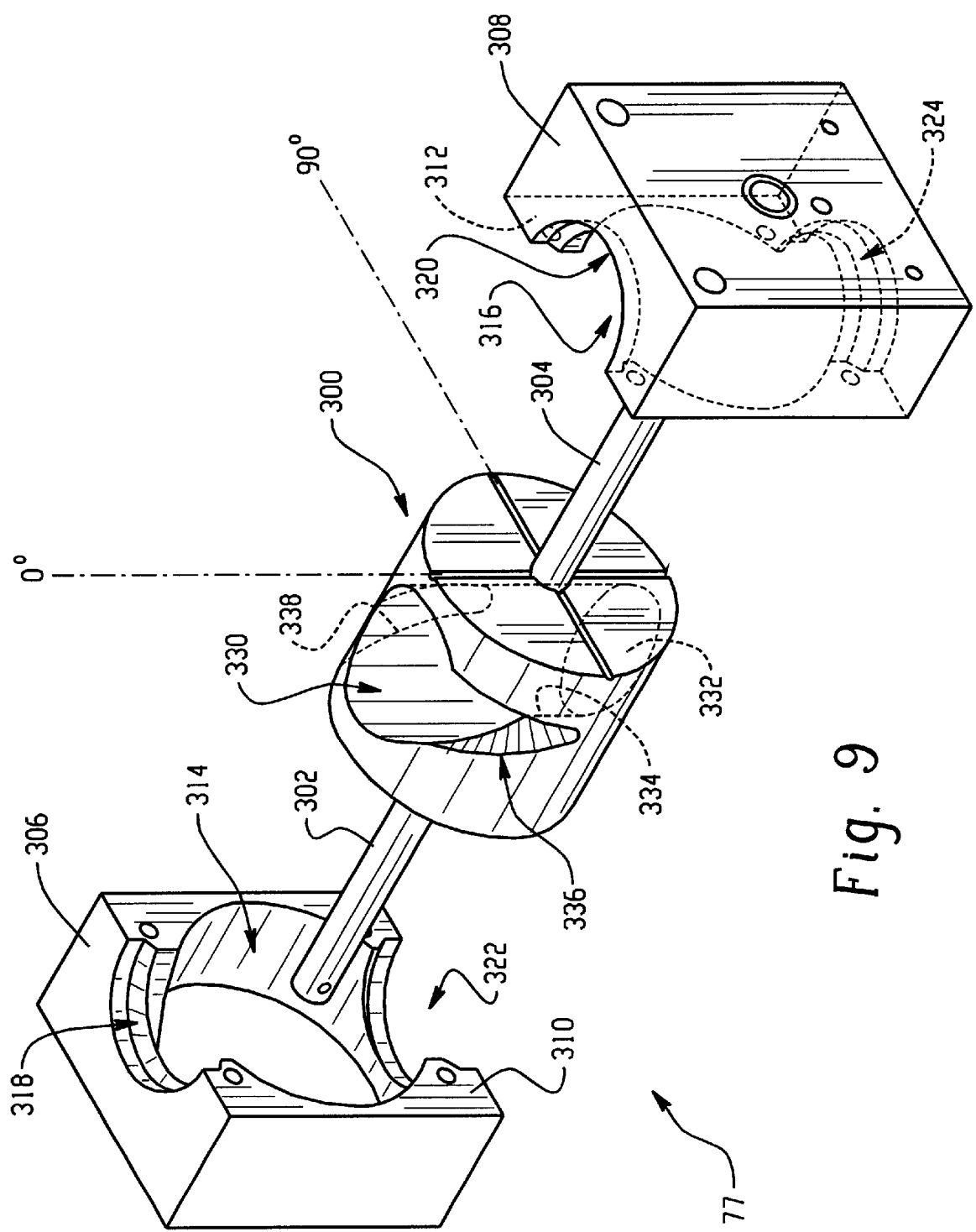
FIG. 9 is an enlarged perspective view of a portion of the apparatus shown in FIG. 8 illustrating the preferred mechanical rotary shutter device for regulating the light intensity in the subject surgical task light system.
Figure 10:
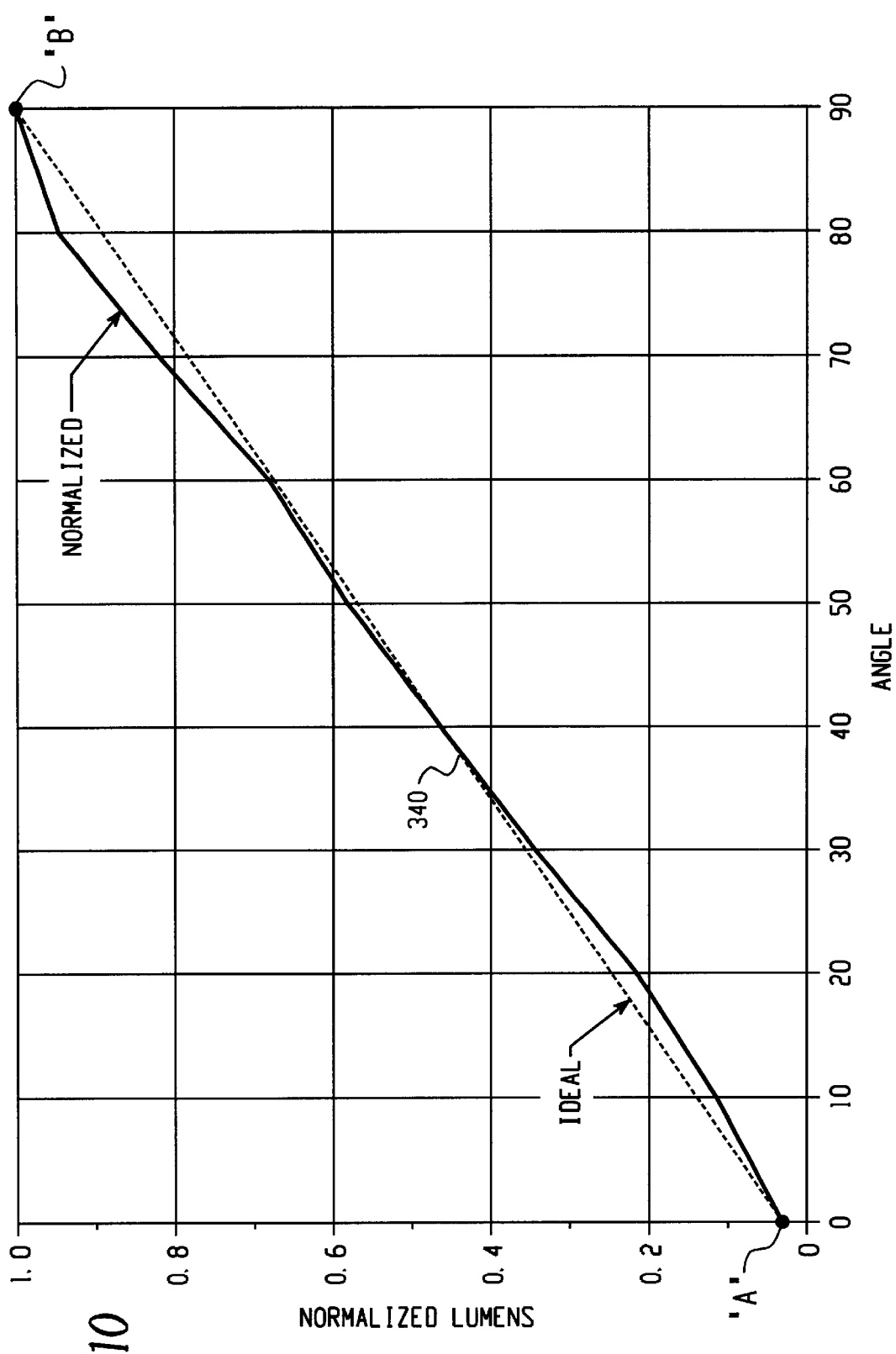
FIG. 10 is a graph illustrating the preferred light intensity curve versus rotary shutter position enabled by the mechanical rotary shutter device shown in FIG. 9.

With reference now to FIGS. 9 and 10, the preferred embodiment of the mechanical shutter device 77 for use in the subject surgical task light system will be described. FIG. 9 is a schematic representation of the mechanical shutter device 77 and FIG. 10 is graphical representation of a shutter light transmission versus shutter position. With reference first to FIG. 9, the mechanical shutter device 77 includes a central substantially cylindrical block member 300 having a pair of outwardly extending axle members 302, 304. The axle members support the block member 300 on a pair of support structures 306, 308, respectively. As shown in the figure, the support structures are illustrated in a spaced apart relationship but, in their assembled state, the face surface 310 of the first support structure 306 engages a corresponding and opposed face surface 312 of the second support structure 308. Suitable fasteners or the like are used to hold the support structures 306, 308 in a connected relationship so that the block member 300 is carried therebetween.

As can be seen from the figure, each of the support structures 306, 308 define a respective central opening 314, 316 adapted to closely receive the block member 300 therein. In addition, each of the support structures 306, 308 define respective light entry opening 318, 320 and light exit openings 322, 324. Preferably, the light entry openings 318, 320 and light exit openings 322, 324 substantially correspond in size to a first light entry opening 330 formed in the block member 300 and a similar light exit opening 332 formed on the opposite side of the block member 300. A central passageway 334 connects the light entry opening 330 with the light exit opening 334. It is to be appreciated, however, that the passageway 332 formed through the block member 300 is not perfectly cylindrical throughout but, rather, includes a pair of V-groove openings 336, 338 formed on opposite sides of the block member 300. Each of the V-groove openings 336, 338 are formed to be contiguous with the central passageway 334. In addition, in accordance with the present invention, the V-groove openings are profiled to take on a particular shape so what, as the light enters the light entry openings 318, 320, the amount of light passing through the block member 300 and out through the light exit openings 322, 324 is precisely controlled based upon the rotational position of the block member 300.

More particularly, in its preferred form, the V-groove openings 336, 338 provide a light transmission versus angular position curve 340 as shown in FIG. 10. When the block member 300 is held in the position shown in FIG. 9 relative to the support structures 306, 308, the light transmission through the mechanical shutter device 77 is substantially at the point in the curve 340 labeled "B". However, when the block member 300 is rotated into the position marked 90° in FIG. 9, the light transmission characteristics of the mechanical shutter device 77 is at curve position "A". In positions therebetween, the light transmission characteristics of the mechanical shutter device 77 substantially follow the curve 340 shown in FIG. 10. It is to be appreciated that the curve is substantially linear relative to angular position of the block member in the support structures.

Figure 11:
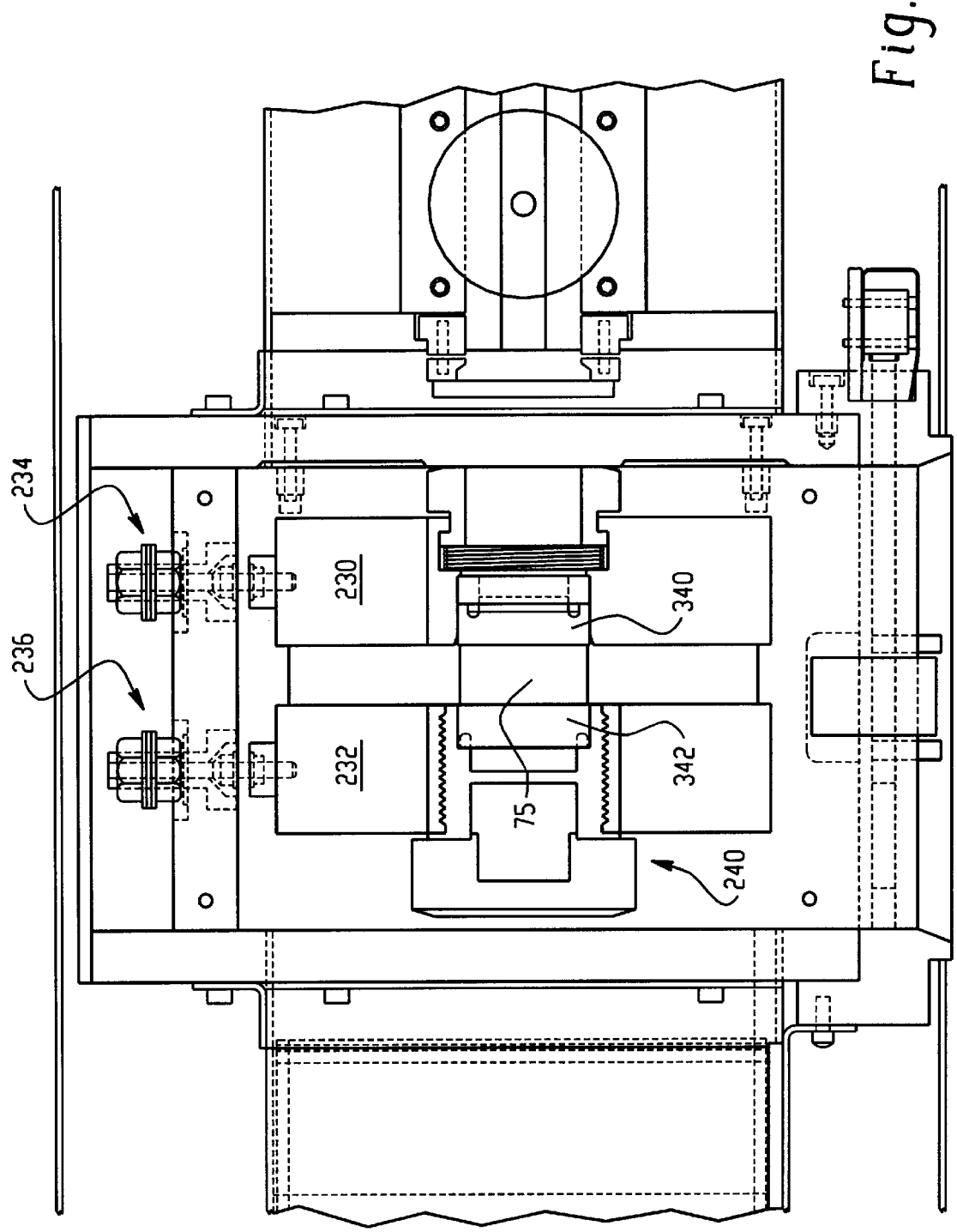
FIG. 11 is an enlarged view of a portion of the illuminator box device shown in FIG. 8 showing the details of a re-lamping module portion thereof.
Figure 12:
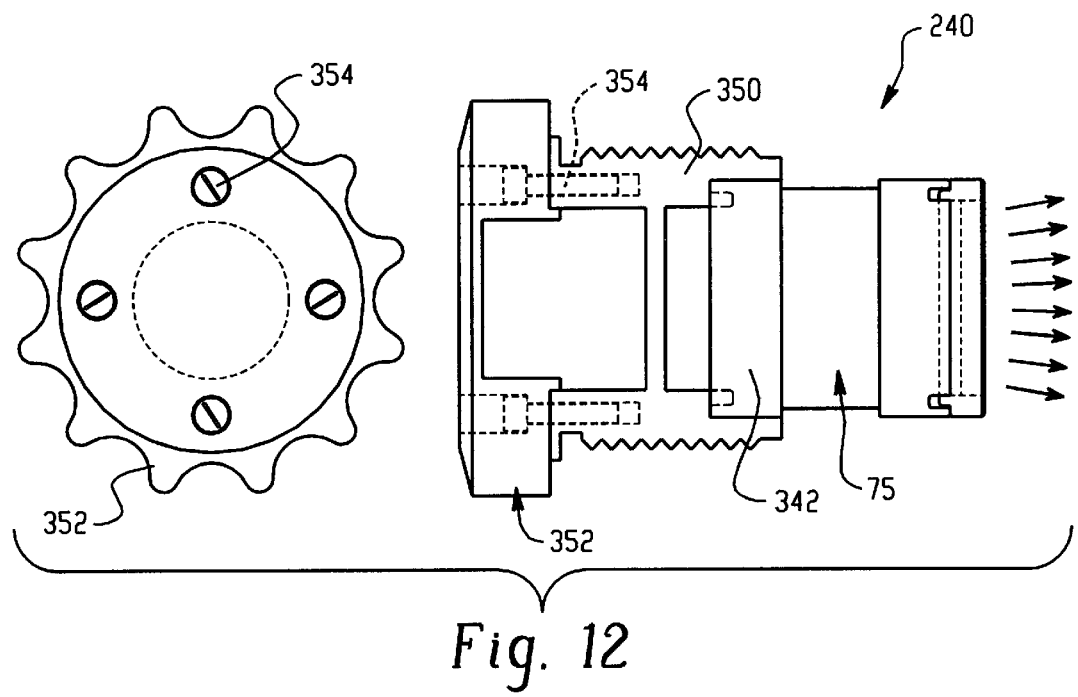
FIG. 12 is an enlarged cross-sectional view of a removable lamp module portion of the re-lamping module shown in FIG. 11.

Turning now the FIGS. 11 and 12, the re-lamping module 76 is shown in greater detail to illustrate the various components thereof and to more completely show the preferred embodiment of the replaceable lamp module 240 formed in accordance with the invention. With reference first to FIG. 11, the replaceable lamp module 240 is illustrated in the position threadedly engaged with a second heat sink 232 in a manner substantially as illustrated in FIG. 8. In the position shown, the first heat sink 230 is connected to a first power connection 234 and the second heat sink 232 is similarly connected to a second power connection 236. Since the heat sinks are aluminum as described above, they conduct electricity from the power connections 234, 236 into a light source 75, preferably a neon arc lamp. The lamp includes first and second electrical connection portions 340, 342 adapted to mechanically engage and electrically connect member 340 to member 230 and member 342 to member 240 via threads 232 and, in turn, with the electrical connectors 234, 236. In that way, power can be delivered to the lamp 75 when the re-lamping module 76 is inserted into the illuminator box device 70 in a position shown in FIG. 11.

FIG. 12 shows the preferred embodiment of the replaceable lamp module 240 formed in accordance with the present invention. As noted above, the replaceable lamp module 240 carries a lamp 75 for threaded engagement with a second heat sink 232. To that end, a replaceable lamp module body 350 is adapted to receive a first end of the lamp therein. Preferably, the body 350 is formed of aluminum or other similar electrically conductive material. In that way, when the body 350 is threaded into the second heat sink 232, an electrical connection is established between the second connection 236 and the conductive portion 342 of the lamp 75.

In order to best help facilitate replacement of the lamp module, a finger wheel 352 is connected to the body using screws 354 or other suitable fasteners. Preferably, the finger wheel is electrically non-conductive and thermally resistant. In that way, the lamp can be easily replaced when the lamp and the body 350 carrying the lamp are hot.

Figure 13A:
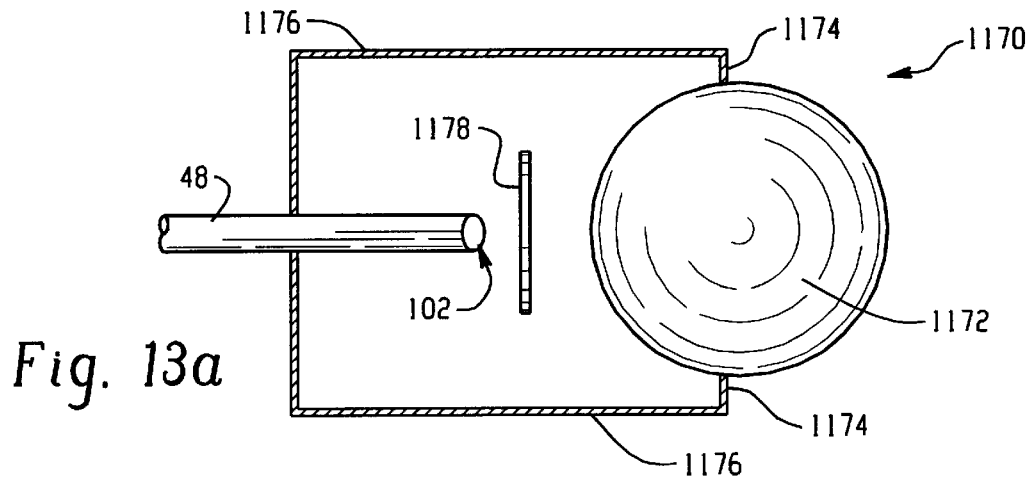
FIGS. 13a and 13b are schematic representations of alternative forms of lensing configurations for use in the manual zoom lens device shown in FIGS. 3–6.

Turning now to FIG. 13a, an alternative optical system 1170 for use in the manual zoom lens device 60 is illustrated. Referring now to that figure, a spherical ball member 1172 formed of a high index of refraction glass is partially embedded within a flexible wall 1174 of a fluid containment vessel 1176 as shown. Disposed within the fluid containment vessel, an iris 1178 is provided as an interface between the ball member 1172 and the distal end 102 of the fiber optic cable 48. Preferably, the fluid containment vessel 1176 is filled with an index matching fluid such as, for example, a silicone oil.

Using the system shown in FIG. 13a, it may be possible to obtain a spot size of between 2–6 inches based on a 1–3 mm range of motion of the ball member relative to the end of the optical fiber. One design parameter of the optical system 1170 that should be observed is that the diameter of the ball member 1172 must be at least four times larger than the diameter of the distal end of the fiber optic cable.

Figure 13B:
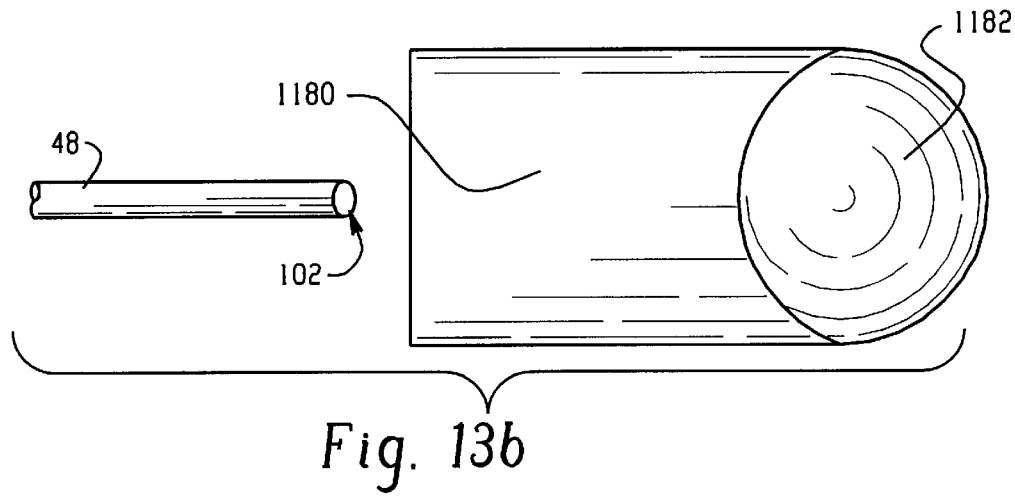

A second alternative lens arrangement is shown in FIG. 13b. A spherical ball 1182, or portion thereof, is bonded to a glass rod 1180. The preferred embodiment of the glass rod is cylindrical, but tapered shapes and shapes with non-circular cross sections, such as a portion of a cone or a square bar may be used. The end of a fiber optic cable 48 is placed near the end of the glass rod and aligned for maximum light transmission. Movement of the end of the glass rod relative to the end of the optical fiber changes the divergence of the light beams exiting the ball and thus the size of the spot created when this device is directed toward a surface. This device might be easier to fabricate and mount than the device shown in FIG. 13a. Furthermore, the use of the glass rod reduces the divergence of the light beam as it travels from the end of the fiber to the exit surface of the glass sphere and thus reduces the overall diameter of the system, thus enabling a practical device of minimal size for use where there is restricted access.

As noted above, a fiber optic commutator is disposed within the mechanical compound joint member 46 to enable the elongate support member 64 to freely rotate through multiple turns along the rotary path identified as B in FIG. 1. A second preferred optical commutator 1200 is shown in FIG. 14.

With reference now to that figure, a substantially cylindrical outer housing member 1202 defines first and second cylindrical engagement surfaces 1204, 1206 adapted to frictionally engage a first and second bearing set 1208, 1210.

A set of first and second interface members 1212, 1214 are provided on opposite sides of the optical commutator 1200 as shown. The first interface member 1212 includes an outer cylindrical engagement area 1220 and an inner precision joint area 1224. The outer cylindrical engagement area 1220 is provided with internal threads 226 adapted to engage a corresponding set of external threads 1228 formed on a cable strain relief member 1230. Functionally, as the cable strain relief member 1230 is threadedly tightened into the outer cylindrical engagement area of the first interface member, the relief member clamps down on the first end 48a of the optical fiber 48 to hold the fiber end in place relative to the first interface member.

The inner precision joint area 1224 of the first interface member 1212 includes a central bore 1232 that is formed to engage the outer surface of the cable end 48a as shown. Preferably, the cable bore 1232 provides a snug fit so that the cable end 48a does not wobble within the first interface member 1212.

In addition to the central bore formed in the inner precision joint area, a bearing interface surface 1234 is formed on the outer portion of the inner precision joint area 1224 as shown. The bearing interface surface 1234 is press fitted into the first bearing set 1208. Thereby, the first interface member 1212 is rotatably held in place within the outer housing member 1202 by the first bearing set 1208.

The second interface member 1214 is formed as a mirror image of the first interface member 1212. Accordingly, the second interface member 1214 includes an outer cylindrical engagement area 1240 and an inner precision joint area 1244. The outer cylindrical engagement area 1240 is provided with internal threads 1246 adapted to engage a corresponding set of external threads 1248 formed on a cable strain relief member 1250. Functionally, as the cable strain relief member 1250 is threadedly tightened into the outer cylindrical engagement area of the second interface member, the relief member clamps down on the second end 48b of the optical fiber 48 to hold the fiber end in place relative to the second interface member.

The inner precision joint area 1244 of the second interface member 1214 includes a central bore 1252 that is formed to engage the outer surface of the cable end 48b as shown. Preferably, the cable bore 1252 provides a snug fit so that the cable end 48b does not wobble within the second interface member 1214.

In addition to the central bore formed in the inner precision joint area, a bearing interface surface 1254 is formed on the outer portion of the inner precision joint area 1244 as shown. The bearing interface surface 1254 is press fitted into the second bearing set 1210. Thereby, the second interface member 1214 is rotatably held in place within the outer housing member 1202 by the second bearing set 1210.

With still yet continued reference to FIG. 14, the first and second ends 48a, 48b of the optical fiber 48 are held in a spaced apart relationship allowing for a small gap 1260 to be formed therebetween. In the preferred embodiment, the gap is about 0.005–0.015 inches. Although it is possible to fill the gap 1260 with an index matching fluid, the optical coupler 1200 preferably uses air as the interface between the first and second optical fiber cable ends 48a, 48b.

A second alternative fiber optic commutator design 1300 is illustrated in FIGS. 15a and 15b. FIG. 15a provides a perspective view of the overall shape of the commutator and FIG. 15b shows the commutator in cross section.

Turning now to those figures, a pair of sealed lens members 1302, 1304 are disposed on opposite sides of a substantially cylindrical housing member 1306 as shown. Generally, the housing member 1306 is comprised of four components including first and second intermatable housing members 1310, 1312, and first and second elongate interface members 1314, 1316. The first elongate interface member 1314 is rotatably contained within the first intermatable housing member 1310. On the other end of the commutator, the second elongate interface member 1316 is rotatably contained within the second intermatable housing member 1312. A set of spaced apart through holes 1320 are provided in the first and second intermatable housing members 1310, 1312 so that the housing members can be connected together using suitable fasteners or the like. In that way, the first and second intermatable housing members are held in place relative to one another.

A set of bearing surfaces 1322, 1324 are formed between the first elongate interface member 1314 and the first intermatable housing member 1310 so that the interface member can rotate freely relative to the housing member 1306. Similarly, a second set of bearing surfaces 1326, 1328 are formed between the second elongate interface member and the second intermatable housing member 1312 to enable the interface member to rotate freely relative to the housing members. The bearing surfaces 1322–1328 can be fashioned from roller or pin bearings or the like.

Lastly in connection with the commutator 1300 illustrated in FIGS. 15a and 15b, the first and second elongate interface members 1314, 1316 are adapted on their outer ends 1330, 1332 for connection to the fiber optic cable ends 48a, 48b. In the embodiment illustrated, the cable ends are connected to the interface members using optically clear adhesives. Index matching fluids can be used in the commutator within the central bores 1334, 1336 formed in the first and second elongate interface members 1314, 1316, respectively. A gasket 1338 is positioned between the contact surfaces of the first and second interface members 1314, 1316 to assist in containing the index matching fluid within the first and second bores 1334, 1336.

Figure 16:
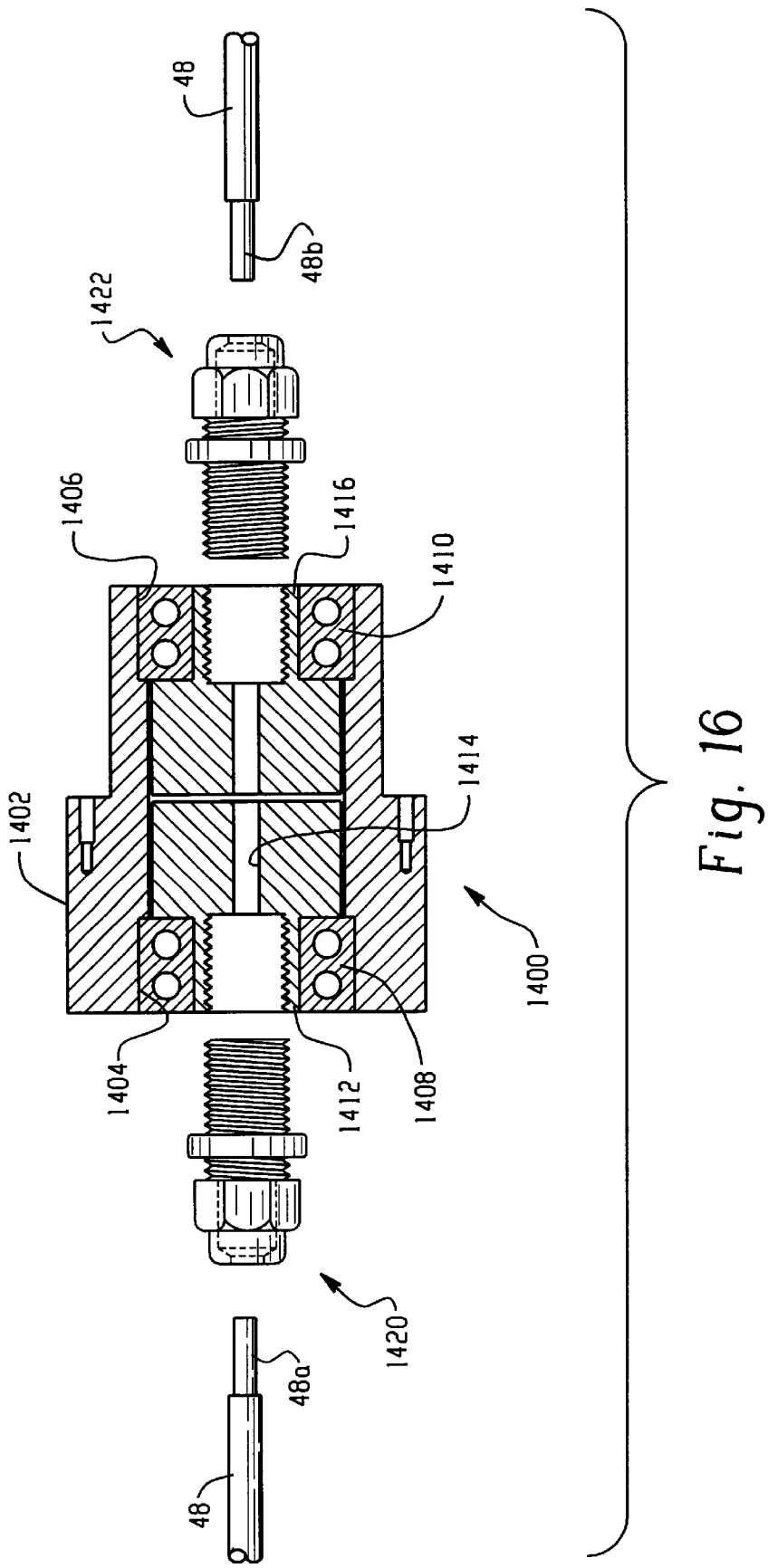
FIG. 16 shows an exploded view in partial cross-sectional of another alternative optical commutator device for use in the subject surgical task light system shown in FIG. 1.

A third alternative fiber optic commutator device 1400 is shown in cross section in FIG. 16. A single solid outer housing member 1402 defines a pair of spaced-apart bearing interface surfaces 1404, 1406 on opposite ends of the housing. A set of first and second ball bearings 1408, 1410 are coaxially carried in the first and second bearing interface surfaces 1404, 1406, respectively.

On the left side of the commutator, a rotatable cable interface member 1412 is held in place by frictional engagement with the bearing 1408. A bore hole 1414 is formed in the cable interface member 1412 so that the free end 48a of the optical cable 48 can be received within the commutator and held in axial alignment with the second free end 48b of the optical cable 48 held in corresponding alignment by a second cable interface member 1416.

The first and second cable interface members 1412, 1416 are each provided with internal threads that are adapted to receive first and second liquid tight fittings 1420, 1422. The liquid tight fittings are standard Heyco fittings commonly available in the industry.

The embodiment illustrated in FIG. 16 allows each of the free ends 48a, 48b of the fiber optic cable 48 to rotate relative to one another as well as relative to the housing member 1402.

Figure 17A:
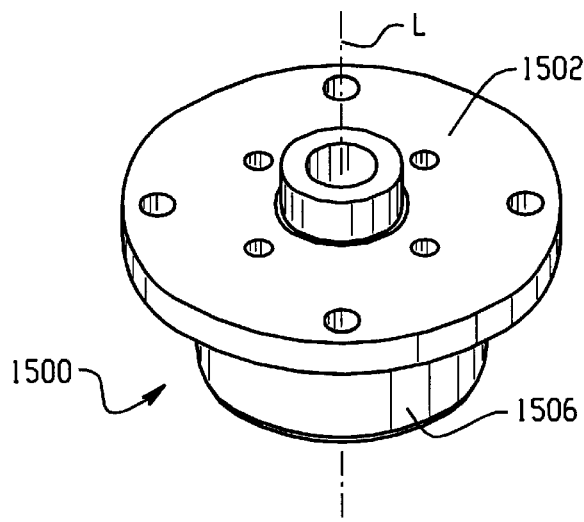
FIGS. 17a–17c show a set of perspective views and a cross-sectional view of another alternative optical commutator device for use in the subject surgical task light system shown in FIG. 1.
Figure 17B:
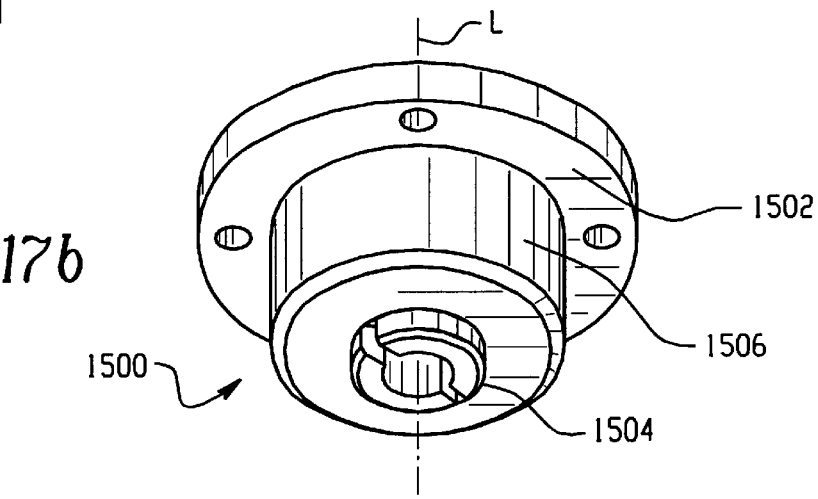
Figure 17C:
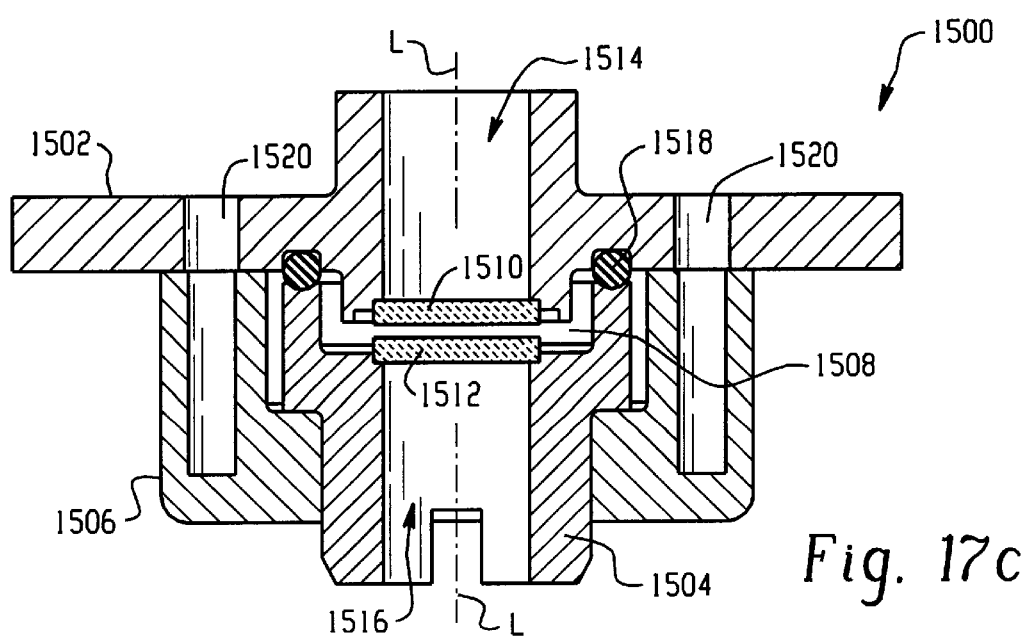

FIGS. 17a–c illustrate a fourth alternative fiber optic commutator embodiment 1500. FIGS. 17a and 17b show the commutator in top and bottom perspective views, respectively, and FIG. 17c is a cross sectional illustration of the commutator.

Referring now to those figures, the commutator 1500 includes a mounting base 1502, a rotator member 1504, and a bearing member 1506. As illustrated, a gap 1508 is formed between the mounting base 1502 and the rotator member 1504. Preferably, an optically clear liquid is contained within the gap 1508. First and second optically clear windows 1510, 1512 are formed in the mounting base 1502 and the rotator member 1504, respectively. The windows prevent the optically clear index matching fluid from flowing into central bores 1514, 1516 formed in the mounting base 1502 and the rotator member 1504, respectively.

As a further measure against leakage and loss of optically clear liquid from the gap 1508, a gasket 1518 member such as, for example, an o-ring, is disposed at the interface between the rotator member 1504 and the mounting base 1502. As shown in FIG. 17c, the o-ring is slightly compressed between the members to ensure a good seal. A set of fasteners 1520 extend through the mounting base and are threadedly received in the bearing member 1506. In the assembled configuration shown in FIG. 17c, the bearing member 1506 is in contact with the mounting base 1502 having the effect of compressing the o-ring 1518 and the rotator member 1504 therebetween. In that way, the rotator member 1504 is held in alignment with the longitudinal axis L defined by the bore holes 1514, 1516. The rotator member 1504 is free to rotate relative to both the bearing member 1506 and the mounting base 1502. The optical cable ends 48a, 48b of the fiber optic cable 48 are received into the bore holes 1514, 1516 and are preferably held fixed in place using an optically clear adhesive material or the like.

Figure 18:
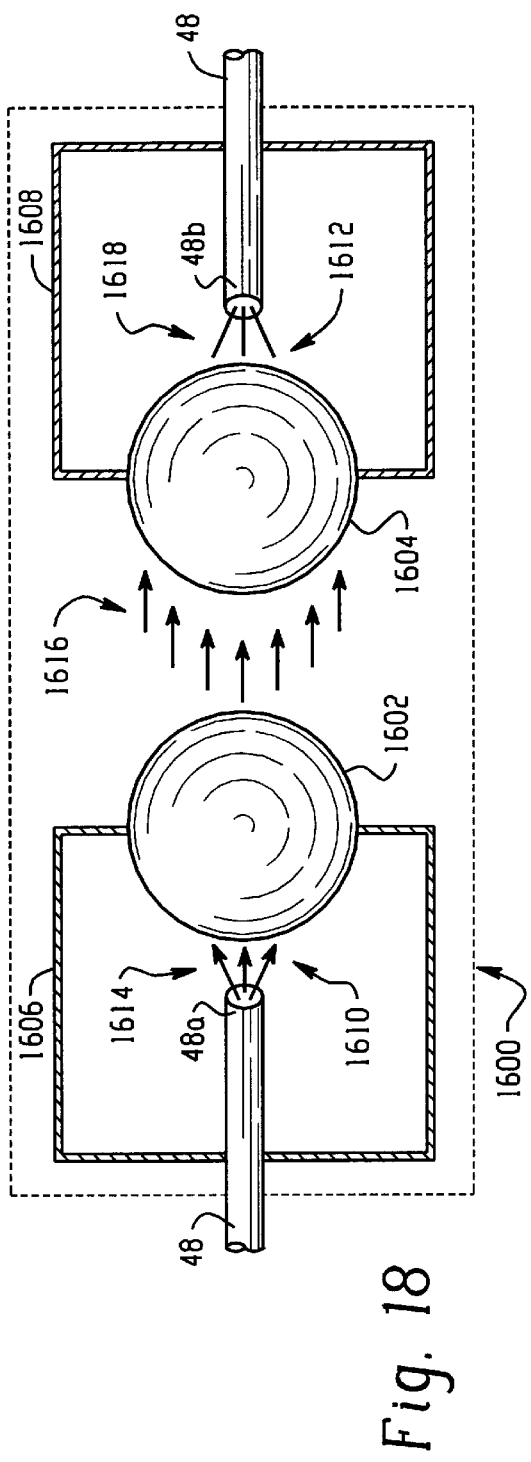
FIG. 18 is a schematic view of yet another alternative optical commutator device for use in the subject surgical task light system shown in FIG. 1; and, FIG. 19 is a schematic view of another alternative optical commutator device for use in the subject surgical task light system shown in FIG. 1.

With reference next to FIG. 18, yet another fiber optic commutator embodiment 1600 is illustrated. As shown there, a pair of spherical high refractive index glass balls 1602, 1604 are each respectively held in a fluid chamber 1606, 1608. The chambers are preferably filled with an index matching fluid such as, for example, a silicone oil. The first distal end 48a of the fiber optic cable 48 is held in alignment adjacent the back end 1610 of the first ball 1602 as shown. Similarly, the second distal end 48b is held in place relative to the back end 1612 of the second ball 1604. As shown, light emitted from the first distal end 48a of the optical fiber forms a divergent light beam 1614 that lands on the back end 1610 of the first ball 1602. The curvature of the first ball causes the divergent light ray 1614 to substantially collimate to form a collimated light beam 1616 in the area between the first and second balls.

The converse of the above occurs in the second ball 1604 as the collimated light beam 1616 is focused on the back end 1612 thereof to form a convergent light beam 1618 having a focal point embedded within the second distal end 48b of the optical fiber cable 48.

In the above embodiment, the first and second chambers 1606, 1608 can be independently rotatably connected to an outer housing member so that the balls 1602, 1604 and cable ends 48a, 48b can rotate freely relative to one another.

Figure 19:
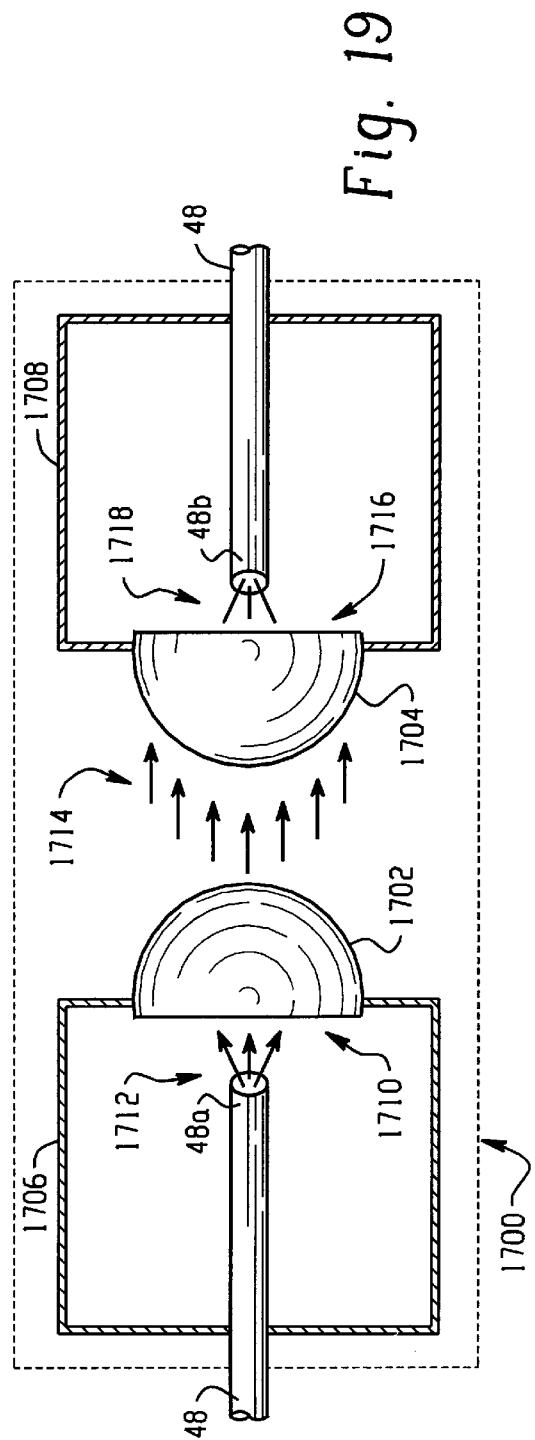

A sixth alternative fiber optic commutator embodiment 1700 is illustrated in FIG. 19. As shown there, a pair of semi-spherical lens members 1702, 1704 are disposed in a corresponding pair of fluid containment chambers 1706, 1708, respectively. Preferably, each of the fluid containment chambers are filled with an index matching fluid such as, for example, a silicone oil.

In the above embodiment, light exiting the first distal end 48a of the fiber optic cable 48 lands on the back side 1710 of the first semi-spherical lens member 1702. The light that exits the first distal end of the fiber optic bundle forms a divergent light ray 1712. The lens 1702 converts the divergent light ray into a substantially collimated beam 1714 in the area between the first and second lens elements.

The converse of the above light ray focusing scheme occurs at the second lens element 1704 whereat the collimated light beam 1714 exits the back end 1716 of the second lens 1704 to form a convergent light beam 1718 as illustrated. Preferably, the focal point of the convergent light beam 1718 is embedded within the second distal end 48b of the fiber optic cable 48.

In the embodiment described above, the first and second fluid containment chambers 1706, 1708 are preferably each independently rotatably connected to an outer housing member to enable the first and second fiber optic cable ends, together with the lens members to freely rotate relative to one another.

The invention has been described in the drawings and above in connection with the preferred embodiments. Obviously, modifications and alterations will occur to others upon a reading and understanding of the description above and the accompanying drawings.

Having thus described the preferred embodiment, the invention is now claimed to be:

1. A surgical task light for use in an associated operating room including a ceiling, a floor, and a table on the floor supporting a patient, the surgical task light comprising:

a light source adapted to generate light;

an elongate optical fiber adapted to conduct said light generated by the light source, the elongate optical fiber having a proximal end for receiving said light generated by said light source and a distal end for emitting said light;

a manually manipulatable support member adapted to support the optical fiber relative to the ceiling of the associated operating room and to hold the distal end of the optical fiber in a plurality of selected positions in close proximity to the patient; and, a manual lens device including a housing carried on an end of the support member adjacent said patient, the manual lens device including at least one lens movable relative to said distal end of the optical fiber based on movement of said housing for focusing the light emitted from the distal end of the optical fiber into a desired selected pattern.

2. The surgical task light according to claim 1 further including an optical commutator for dividing the elongate optical fiber into first and second portions, the optical commutator enabling relative movement between the first and second portions for providing an increased range of movement in said support member.

3. The surgical task light according to claim 1 further including a shutter device operatively associated with said light source for controlling an amount of said light delivered from said light source to said lens device.

4. The surgical task light according to claim 1 wherein said support member includes an elongate gooseneck portion carrying said lens device and formed of a plurality of interlocking joint members, the gooseneck portion being manually manipulatable into a plurality of selected orientations and being adapted to hold a position in said plurality of selected orientations to hold the lens device stationary against a force of gravity at a selected position.

5. A surgical task light for use in an associated operating room including a ceiling, a floor, and a table on the floor supporting a patient, the surgical task light comprising:

a light source adapted to generate light, the light source including a re-lamping module comprising a replaceable light bulb module and a set of heat sink members carrying the replaceable light bulb module, the set of heat sink members being adapted to conduct heat from said replaceable light bulb module and to conduct electrical power to said replaceable light bulb module;

an elongate optical fiber adapted to conduct said light generated by the light source, the elongate optical fiber having a proximal end for receiving said light generated by said light source and a distal end for emitting said light;

a support member adapted to support the optical fiber relative to the ceiling of the associated operating room and to hold the distal end of the optical: fiber in a plurality of selected positions; and, a lens device carried on an end of the support member adjacent said patient, the lens device transmitting said light emitted from the distal end of the optical fiber through the lens device and focusing the light emitted from the distal end of the optical fiber into a desired selected pattern.

6. The surgical task light according to claim 5 wherein said replaceable light bulb module includes:

an electrically conductive main body member adapted for selective connection to at least one of said set of heat sink members;

a light bulb carried on said electrically conductive main body member; and, a manual grip portion formed of a thermally resistive material for providing a manually grippable surface for selective manual removal of said replaceable light bulb module from said light source.

7. The surgical task light according to claim 3 wherein said shutter device includes a rotatable cylindrical member defining a tapered passageway opening for delivering said light from the light source to said lens device in an amount based on a rotational position of said cylindrical member.

8. The surgical task light according to claim 7 wherein said amount of said light delivered to said lens device is substantially linearly related to said rotational position of said cylindrical member.

9. A surgical task light for use in an associated operating room including a ceiling, a floor, and a table on the floor supporting a patient, the surgical task light comprising:

a light source adapted to generate light,;

an elongate optical fiber adapted to conduct said light generated by the light source, the elongate optical fiber having a proximal end for receiving said light generated by said light source and a distal end for emitting said light;

a support member adapted to support the optical fiber relative to the ceiling of the associated operating room and to hold the distal end of the optical fiber in a plurality of selected positions relative to the patient; and, a lens device carried on an end of the support member adjacent said patient, the lens device transmitting said light emitted from the distal end of the optical fiber through the lens device and focusing the light emitted from the distal end of the optical fiber into a desired selected pattern, wherein said light source includes:

a light bulb disposed adjacent said proximal end of said elongate optical fiber, the light bulb, the proximal end of the elongate optical fiber, and a space therebetween defining a light path; and, a cooling system for cooling the light bulb, the cooling system defining an air duct for directing an air flow through the light source, the air duct being separated from said light path to prevent said air flow from entering into said light path.

10. The surgical task light according to claim 1 in combination with:

a sterile sheath member, the sterile sheath member including a transparent portion adapted to transmit light therethrough and an elongate substantially tubular cover member connected on one end to the transparent portion, the sterile sheath member being adapted for connection onto said surgical task light with the transparent portion disposed adjacent said lens device and said tubular cover member selectively extendable over said support member.

11. A surgical task light system comprising:

a light source adapted to generate light;

an elongate optical fiber adapted to carry said light generated by the light source, the elongate optical fiber having a proximal end for receiving said light generated by said light source and a distal end for emitting said light;

a manually operable support member adapted to support the optical fiber relative to a ceiling of an associated operating room and to hold the optical fiber in a plurality of selected positions;

a manually adjustable lens device carried on the support member and passing said light emitted from said distal end of the optical fiber through the lens device for focusing the light emitted from the distal end of the optical fiber into a desired selected pattern; and, a re-lamping module including a replaceable light bulb module and a set of heat sink members carrying the replaceable light bulb module, the set of heat sink members being adapted to conduct heat from said replaceable light bulb module and to conduct electrical power to said replaceable light bulb module.

12. The re-lamping module according to claim 11 wherein said replaceable light bulb module includes:

an electrically conductive main body member adapted for selective connection to at least one of said set of heat sink members;

a light bulb carried on said electrically conductive main body member; and, a main grip portion formed of a thermally resistive material for providing a manually grippable surface for selective manual removal of said replaceable light bulb module from said light source of the surgical task light.

13. The surgical task light according to claim 5 wherein:

the light source further includes a housing; and, the re-lamping module is selectively movable relative to the housing to facilitate replacement of said light bulb module.

14. The surgical task light according to claim 5 wherein the replaceable light bulb module includes:

at least one light bulb; and, a manual grip portion providing a surface for selective manual removal of the replaceable light bulb module from said light source.

15. The surgical task light according to claim 9 wherein said air duct is separated from said light path to completely prevent said air flow from entering into said light path.

16. The re-lamping module according to claim 11 wherein:

the light source includes a housing; and, the re-lamping module is selectively movable relative to the housing to facilitate replacement of said light bulb nodule.

17. The re-lamp module according to claim 11 wherein the replaceable light bulb module includes:
- at least one light bulb; and,
- a manual grip portion providing a surface for selective manual removal of the replaceable light bulb module from the light source.

18. A surgical task light system comprising:
- a light source adapted to generate light;
- an elongate optical fiber adapted to carry said light generated by the light source, the elongate optical fiber having a proximal end for receiving said light generated by said light source and a distal end for emitting said light;
- a manual support member adapted to support the optical fiber relative to a ceiling of an associated operating room and to hold the optical fiber in a plurality of manually selectable positions;
- a lens device carried on the manual support member and transmitting said light emitted from said distal end of the optical fiber through the lens device, the lens device focusing the light emitted from the distal end of the optical fiber into a desired selected pattern, and;
- a sterile sheath member including a transparent portion adapted to transmit said light therethrough and an elongate substantially tubular cover member connected on one end to the transparent portion, the sterile sheath member being adapted for connection onto said surgical task light with the transparent portion disposed adjacent said lens device and said tubular cover member selectively extendable over said support member.

19. A surgical task light system comprising:
- a light source with a bulb adapted to generate light along a light path;
- an elongate optical fiber adapted to carry said light generated by the bulb, the elongate optical fiber having a proximal end disposed adjacent to said bulb for receiving said light and a distal end for emitting said light;
- a support member adapted to support the optical fiber relative to a ceiling of an associated operating room and to hold the optical fiber in a plurality of manually selectable positions;
- a lens device carried on the manual support member, the lens device conducting said light emitted from the distal end of the optical fiber and focusing the light emitted from the distal end of the optical fiber into a desired selected pattern; and,
- a cooling system for cooling the bulb, the cooling system including an air duct for directing an air flow through said light source, the air duct being separated from said light path to substantially prevent said air flow from entering into said light path.

20. The cooling system according to claim 19 wherein said air duct is separated from said light path to completely prevent said air flow from entering into said light path.

21. The surgical task light according to claim 5 further including an optical commutator for dividing the elongate optical fiber into first and second portions, the optical commutator enabling relative movement between the first and second portions for providing an increased range of movement in said support member.

22. The surgical task light according to claim 5 further including a shutter device operatively associated with said light source for controlling an amount of said light delivered from said light source to said lens device.

23. The surgical task light according to claim 22 wherein said shutter device includes a rotatable cylindrical member defining a tapered passageway opening for delivering said light from the light source to said lens device in an amount based on a rotational position of said cylindrical member.

24. The surgical task light according to claim 23 wherein said amount of said light delivered to said lens device is substantially linearly related to said rotational position of said cylindrical member.

25. The surgical task light according to claim 5 wherein said support member includes an elongate gooseneck portion carrying said lens device and formed of a plurality of interlocking joint members, the gooseneck portion being manually manipulatable into a plurality of selected orientations and being adapted to hold a position in said plurality of selected orientations to hold the lens device stationary against a force of gravity at a selected position.

26. The surgical task light according to claim 5 in combination with:
- a sterile sheath member, the sterile sheath member including a transparent portion adapted to transmit light therethrough and an elongate substantially tubular cover member connected on one end to the transparent portion, the sterile sheath member being adapted for connection onto said surgical task light with the transparent portion disposed adjacent said lens device and said tubular cover member selectively extendable over said support member.

27. The surgical task light according to claim 9 further including an optical commutator for dividing the elongate optical fiber into first and second portions, the optical commutator enabling relative movement between the first and second portions for providing an increased range of movement in said support member.

28. The surgical task light according to claim 9 further including a shutter device operatively associated with said light source for controlling an amount of said light delivered from said light source to said lens device.

29. The surgical task light according to claim 28 wherein said shutter device includes a rotatable cylindrical member defining a tapered passageway opening for delivering said light from the light source to said lens device in an amount based on a rotational position of said cylindrical member.

30. The surgical task light according to claim 29 wherein said amount of said light delivered to said lens device is substantially linearly related to said rotational position of said cylindrical member.

31. The surgical task light according to claim 9 wherein said support member includes an elongate gooseneck portion carrying said lens device and formed of a plurality of interlocking joint members, the gooseneck portion being manually manipulatable into a plurality of selected orientations and being adapted to hold a position in said plurality of selected orientations to hold the lens device stationary against a force of gravity at a selected position.

32. The surgical task light according to claim 9 in combination with:
- a sterile sheath member, the sterile sheath member including a transparent portion adapted to transmit light therethrough and an elongate substantially tubular cover member connected on one end to the transparent portion, the sterile sheath member being adapted for connection onto said surgical task light with the transparent portion disposed adjacent said lens device and said tubular cover member selectively extendable over said support member.

* * * * *